United States Patent
Balasubramanian et al.

(10) Patent No.: US 7,092,110 B2
(45) Date of Patent: Aug. 15, 2006

(54) OPTIMIZED MODEL AND PARAMETER SELECTION FOR OPTICAL METROLOGY

(75) Inventors: Raghu Balasubramanian, Santa Clara, CA (US); Sanjay Yedur, San Ramon, CA (US); Vi Vuong, Fremont, CA (US); Nickhil Jakatdar, Los Altos, CA (US)

(73) Assignee: Timbre Technologies, Inc., Santa Clara, CA (US)

( * ) Notice: Subject to any disclaimer, the term of this patent is extended or adjusted under 35 U.S.C. 154(b) by 79 days.

(21) Appl. No.: 10/397,631

(22) Filed: Mar. 25, 2003

(65) Prior Publication Data

US 2004/0017575 A1    Jan. 29, 2004

Related U.S. Application Data

(63) Continuation-in-part of application No. 10/206,491, filed on Jul. 25, 2002.

(51) Int. Cl.
*G01B 11/14* (2006.01)
*G01B 7/00* (2006.01)
*G01N 21/86* (2006.01)
*G01R 31/26* (2006.01)

(52) U.S. Cl. ............ 356/625; 250/559.22; 702/155; 438/16

(58) Field of Classification Search ............ 356/2, 356/388–398, 625–640, 399–401; 353/5, 353/26; 378/26; 250/559.11, 559.01–559.07, 250/559.19–559.24, 559.26, 559.27, 548; 703/2, 13; 700/95, 97, 98, 103, 117–121, 700/2, 13; 716/1, 4, 19–21; 438/5, 7–9, 438/14, 16; 702/189, 81, 82, 117, 155–159, 702/166, 167–170; 355/53, 55, 77; 430/5, 430/22, 30
See application file for complete search history.

(56) References Cited

U.S. PATENT DOCUMENTS

| 5,326,659 | A | * | 7/1994 | Liu et al. ............... 430/5 |
| 5,719,796 | A | * | 2/1998 | Chen ............... 703/13 |
| 5,805,290 | A | | 9/1998 | Ausschnitt et al. |
| 5,963,329 | A | * | 10/1999 | Conrad et al. ....... 356/613 |
| 6,130,750 | A | | 10/2000 | Ausschnitt et al. |
| 6,317,211 | B1 | | 11/2001 | Ausschnitt et al. |

(Continued)

OTHER PUBLICATIONS

International Search Report mailed Mar. 17, 2004, for PCT patent application No. PCT/US03/23281 filed Jul. 25, 2003, 4 pages.

(Continued)

*Primary Examiner*—Gregory J. Toatley, Jr.
*Assistant Examiner*—Gordon J. Stock, Jr.
(74) *Attorney, Agent, or Firm*—Morrison&Foerster LLP

(57) ABSTRACT

A profile model for use in optical metrology of structures in a wafer is selected based on a template having one or more parameters including characteristics of process and modeling attributes associated with a structure in a wafer. The process includes performing a profile modeling process to generate a profile model of a wafer structure based on a template having one or more parameters including characteristics of process and modeling attributes. The profile model includes a set of geometric parameters associated with the dimensions of the structure. The generated profile model may further be tested against termination criteria and the one or more parameters modified. The process of performing a modeling process to generate a profile model and testing the generated profile model may be repeated until the termination criteria are met.

46 Claims, 20 Drawing Sheets

U.S. PATENT DOCUMENTS

| | | | |
|---|---|---|---|
| 6,334,209 B1 * | 12/2001 | Hashimoto et al. | 716/21 |
| 6,470,230 B1 | 10/2002 | Toprac et al. | |
| 6,532,428 B1 | 3/2003 | Toprac | |
| 6,609,086 B1 | 8/2003 | Bao et al. | |
| 6,622,059 B1 | 9/2003 | Toprac et al. | |
| 6,704,661 B1 | 3/2004 | Opsal et al. | |
| 6,748,104 B1 * | 6/2004 | Bachelder et al. | 382/151 |
| 6,778,911 B1 * | 8/2004 | Opsal et al. | 702/27 |
| 6,867,866 B1 * | 3/2005 | Chang et al. | 356/446 |

OTHER PUBLICATIONS

International Search Report mailed Feb. 18, 2005, for PCT patent application No. PCT/US2004/009453, filed Mar. 25, 2004, 4 pages.

* cited by examiner

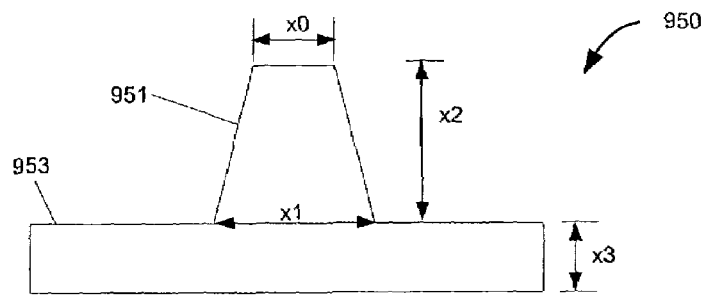
FIGURE 10A
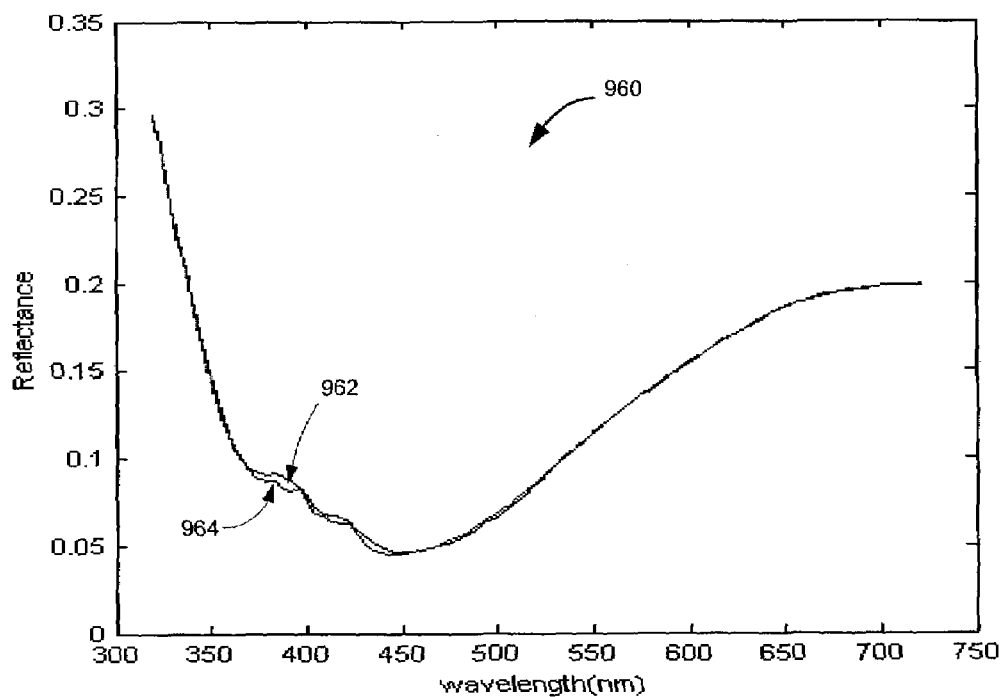
FIGURE 10B
| 3 Sigma Confidence Interval | | | |
|---|---|---|---|
| X0 | X1 | X2 | X3 |
| 1.99 | 1.95 | 0.89 | 0.30 |
GOF = 0.9990
FIGURE 10C

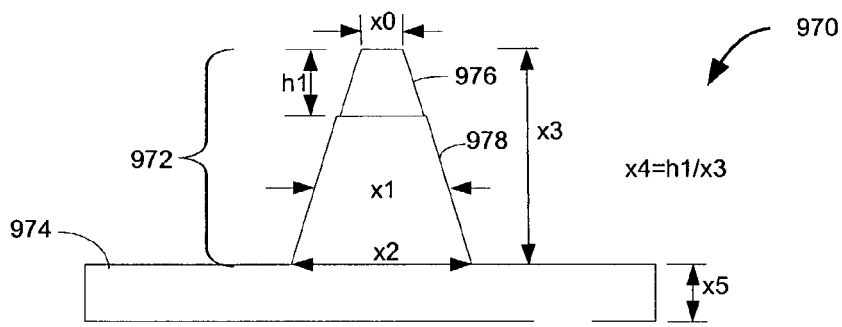
FIGURE 11A
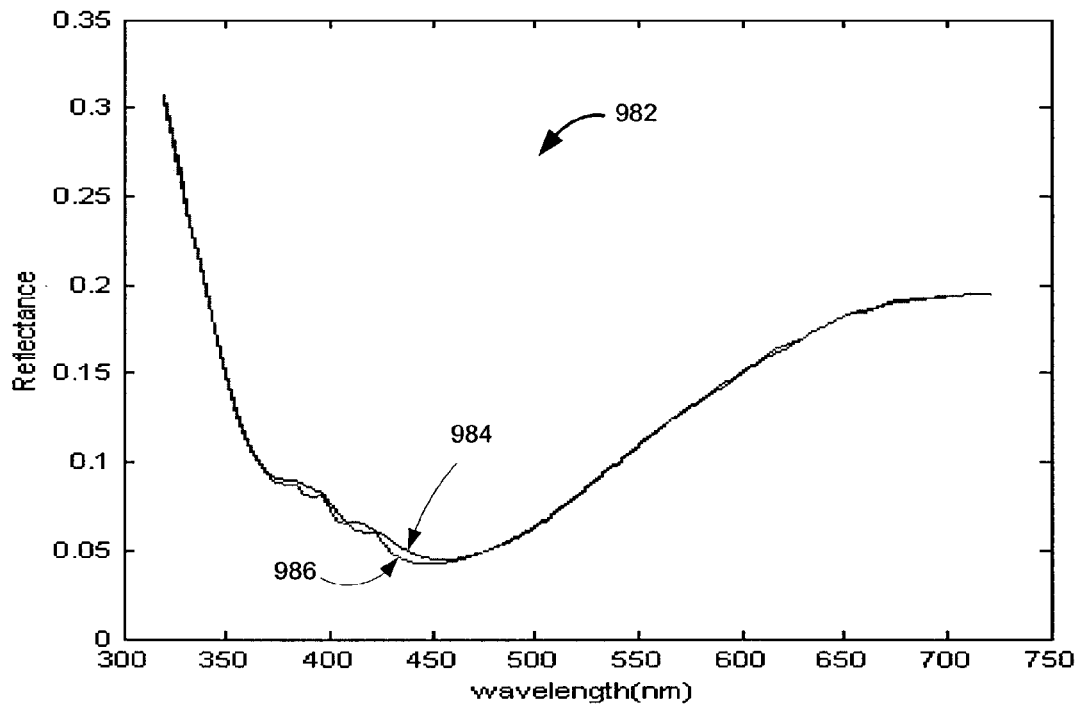
FIGURE 11B
```
3 Sigma Confidence Interval
----------------------------------------------------------
 X0    X1    X2    X3    X4    X5
6.81  17.92  2.54  0.55  17.26  0.09
GOF = 0.9994
```
FIGURE 11C

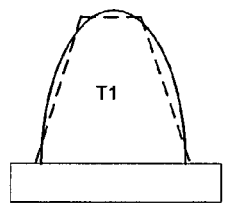
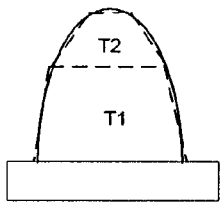
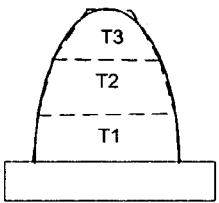
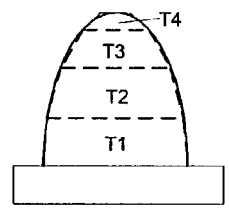
FIGURE 13A  FIGURE 13B  FIGURE 13C  FIGURE 13D
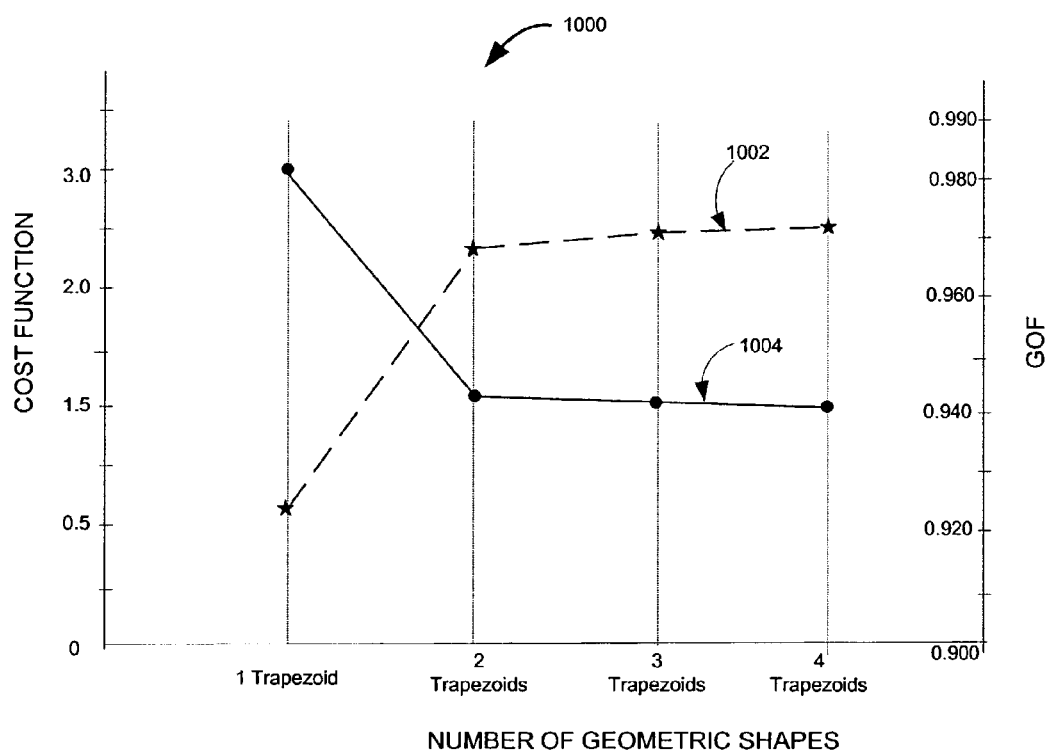
FIGURE 13E Recommended Actions:
1. Alter the geometrical model from 1 trapezoid to 2 trapezoids.
2. Convert parameters with correlation of .9XX from variable to fixed.
3. Use only wavelengths that provide an "acceptable" noise signal.
4. Float parameter X.
.
.
.
n

OPTIMIZED MODEL AND PARAMETER SELECTION FOR OPTICAL METROLOGY

CROSS-REFERENCE TO RELATED APPLICATIONS

This application is a continuation-in-part of, and claims benefit to, co-pending U.S. patent application Ser. No. 10/206,491, entitled "MODEL AND PARAMETER SELECTION FOR OPTICAL METROLOGY" by Vuong, et al., filed on Jul. 25, 2002, which is incorporated herein by reference.

BACKGROUND OF INVENTION

1. Field of Invention

This application relates generally to integrated circuit (IC) metrology, and more particularly to the selection of a structure model and parameters for optical metrology using a template with expected parameter values and/or value ranges.

2. Related Art

With the current drive towards smaller geometries of IC devices, measurement of IC device features is increasingly difficult as the size of the features become smaller. One method of measuring the features involves the use of gratings or periodic structures formed in test areas of a wafer that are proximate to or within the devices or circuits on the wafer. Knowledge of the dimensions of the gratings or periodic structures is essential in order to determine if the dimensions of the structure are within acceptable ranges and if, for example, a particular fabrication process causes the sidewalls of the features to be tapered, vertical, T-topped, undercut, or have footings.

Measurement of the periodic structure features may be done with a scanning electron microscope (SEM) or similar device where the sample is cleaved and examined. The cross-section SEM method is typically slow, expensive, destructive, and typically only provides one measurement number seen from the top of the feature.

Another measurement technique uses scatterometry. In scatterometry, spectroscopic reflectometry and ellipsometry, multiple-angle-of-incidence (MAI) devices, and mixed design systems are typically used to shine light on the structure and measure the reflected light. Empirical scatterometry basically uses an approach where the diffraction signals are measured for known widths of features of a structure, the pair of diffraction signals and structure widths used to create a library. Even for a limited library of structure dimensions and associated diffraction signals, the empirical scatterometry technique for building a library is time consuming and expensive. As the resolution of the structure dimension increases, the size of the library increases while the time to create and use the library increases considerably.

In another measurement technique, instead of using a library of diffraction signals and profile data, regression is used to determine the profile data from the measured diffraction signal. In using regression, one or more optimization techniques may be used to determine the profile data from the measured diffraction signal.

The length of time needed to create a library or to make a regression result converge varies depending on the profile model used and the number of parameters used to represent the profile model in the diffraction signal calculations. Typically, the more complicated the profile model and the more parameters used, the more time and/or computing resources needed to retrieve the desired information from measurements. Further, depending on the skill and/or experience of a particular operator the process for creating a library may vary in time, and the final parameter selection and profile model may vary considerably.

SUMMARY OF INVENTION

In an exemplary embodiment, a profile model for use in optical metrology of structures in a wafer is selected based on characteristics of the process and/or modeling attributes of the structure included in a template associated with the structure in the wafer. The process includes selecting a template associated with a wafer structure and having one or more parameters including characteristics of process and modeling attributes of the wafer structure. A profile modeling process is then performed to generate a profile model for use in optical metrology of the wafer structure. The profile model is based, at least in part, on the one or more parameters of the selected template associated with the wafer structure. In one example of one aspect, the generated profile model may further be tested against one or more termination criteria. The one or more parameters may be modified and the process of performing a modeling process to generate a profile model and testing the generated profile model repeated until the one or more termination criteria are met.

According to another aspect of an exemplary embodiment, the process may further include generating a list of actions to improve the profile model. The actions may include modifying one or more of the parameters or selecting a new template associated with the wafer structure. The actions may be chosen manually, automatically, or any combination of the two.

BRIEF DESCRIPTION OF DRAWINGS

FIG. 10A is an exemplary diagram of a wafer structure model using a rectangle and one trapezoid.

FIG. 10B is an exemplary reflectance graph of two highly correlated parameters of a wafer structure model using a rectangle and one trapezoid.

FIG. 10C is a table illustrating goodness of fit (GOF) and the confidence interval of each parameter of the model using a rectangle and one trapezoid.

FIG. 11A is an exemplary diagram of a wafer structure model using a rectangle and two trapezoids.

FIG. 11B is an exemplary reflectance graph of two highly correlated parameters of a wafer structure model using a rectangle and two trapezoids.

FIG. 11C is a table illustrating the goodness of fit (GOF) and confidence interval of each parameter of the profile model using a rectangle and two trapezoids.

FIGS. 13A to 13D are exemplary profile models using from one to four trapezoids to model a wafer structure.

FIG. 13E is an exemplary graph of the cost function and GOF of simulated signal versus the measured signal as a function of the number of trapezoids used in the profile model.

DETAILED DESCRIPTION OF EXEMPLARY EMBODIMENTS

The following description is presented to enable any person skilled in the art to make and use the invention. Descriptions of specific materials, techniques, and applications are provided only as examples. Various modifications to the examples described herein will be readily apparent to those skilled in the art, and the general principles defined herein may be applied to other examples and applications without departing from the spirit and scope of the invention. Thus, the present invention is not intended to be limited to the examples described and shown, but is to be accorded a scope consistent with the appended claims.

In order to facilitate the description of the certain aspects of various embodiments, either an ellipsometric or reflectometric optical metrology system is used to illustrate certain concepts and principles. Graphs of diffraction signals off wafer structures using an ellipsometer, e.g., cos (Δ) and tan (Ψ), will be utilized to describe certain exemplary embodiments while reflectometric reflectance graphs will be utilized to describe others. It is understood that the same concepts and principles equally apply to ellipsometric, reflectometric, or other optical metrology systems suitable for IC metrology.

Figure 1:
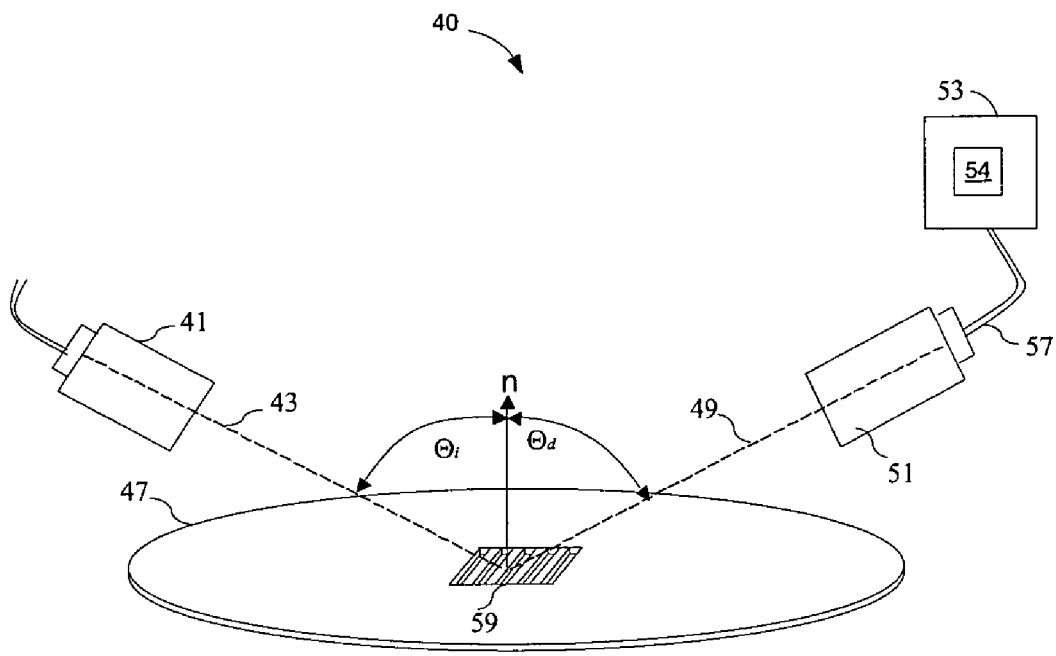
FIG. 1 is an architectural diagram illustrating the use of optical metrology to measure the diffraction signals off wafer periodic structures.

FIG. 1 is an architectural diagram illustrating the use of optical metrology to measure the diffraction signals off structures patterned on a wafer. The optical metrology system 40 includes a metrology beam source 41 projecting a beam 43 at the target structure 59 of a wafer 47. The metrology beam 43 is projected at an incidence angle $\theta_i$ towards the target structure 59 and diffracted at a diffraction angle $\theta_d$ with respect to normal n. The diffraction beam 49 is measured by a metrology beam receiver 51. The diffraction beam data 57 is transmitted to a profile application server 53. The profile application server 53 compares the measured diffraction beam data 57 against a library 54 of calculated diffraction beam data representing varying combinations of critical dimensions of the target structure and resolution of the critical dimensions. In one exemplary embodiment, the library instance in library 54 best matching the measured diffraction beam data 57 is selected. The profile and associated critical dimensions of the selected library instance may provide a two-dimensional or three-dimensional representation of the target structure. The optical metrology system 40 may utilize a reflectometer, an ellipsometer, or other optical metrology device to measure the diffraction beam or signal. An exemplary optical metrology system is described in co-pending U.S. patent application Ser. No. 09/727,530 entitled "System and Method for Real-Time Library Generation of Grating Profiles" by Jakatdar, et al., filed on Nov. 28, 2000, and is incorporated in its entirety herein by reference.

Figure 2:
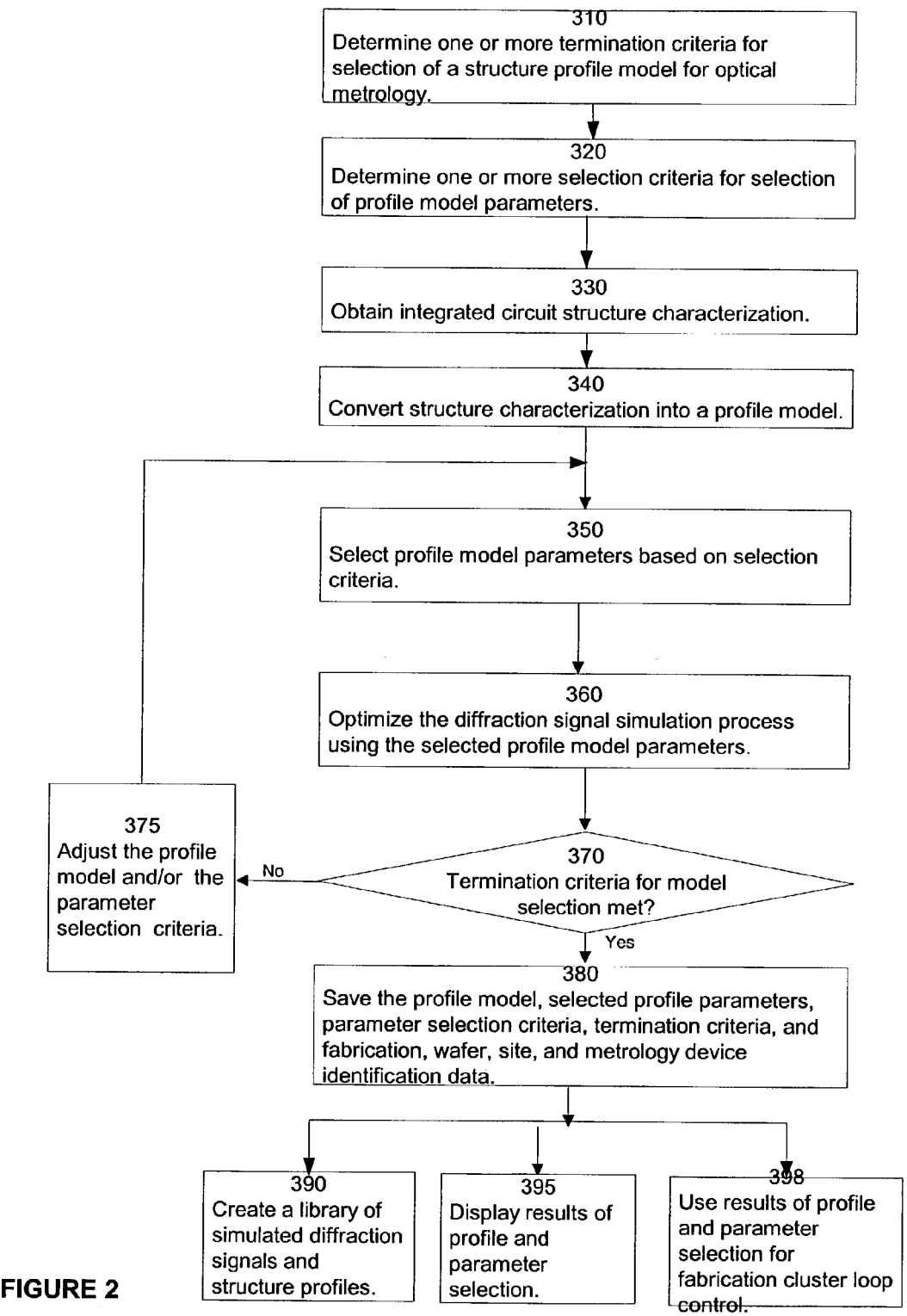
FIG. 2 is an exemplary flowchart of the overall process for model and parameter selection for optical metrology of integrated circuit structures.

FIG. 2 is a flowchart of an exemplary process for model and parameter selection for optical metrology of wafer structures. In step 310, one or more termination criteria for selection of a structure profile model are determined. A termination criterion is a yardstick against which the result of the selection process is measured. The termination criteria may include a cost function value, a Goodness-of-Fit (GOF) value, and/or other curve fitting metrics, as well as confidence intervals of parameters measured.

For example, a cost function between a simulated signal off the structure using the profile model parameters compared to a measured signal may be used as a termination criterion. One cost function comparison is illustrated by the equations below, where $V_1$ and $V_2$ are two vectors of size n, and the cost function of $V_1$ relative to $V_2$ is:

$$\text{Cost}(V_1, V_2) = \left( \sum_{i=1}^{n} (V_{1i} - V_{2i})^p \right)^{1/p} \quad (1.00)$$

where i represents the i th member of the vector and p is an arbitrary number associated with the metric. The first vector is the set of signal values at measurement points for the metrology device used and the second vector is the corresponding set of simulated signal values at the same points. A cost function termination criterion may be set at a specific number, for example, 0.25.

Another exemplary termination criterion may be the goodness of fit (GOF) between the graph of the measured and simulated signal values. The GOF is a measure of the proximity of two sets of values. For example, when ellipsometric measurements are used, GOF is based on values for tan ψ and cos Δ, where tan ψ and cos Δ are represented by a single vector of n dimensions:

$$S = [\tan \psi_1 \tan \psi_2 \ldots \tan \psi_{n/2} \cos \Delta_1 \cos \Delta_2 \ldots \cos \Delta_n] \quad (1.10)$$

One commonly used formula for GOF between a measured signal $S_m$ compared to a simulated signal $S_s$ is:

$$GOF = 1 - \frac{\sum_i^n (S_s(i) - S_m(i))^2}{\sum_i^n (S_m(i) - \overline{S}_m)^2} \text{ where} \quad (2.00)$$

$$\overline{S}_m = \frac{\sum_i^n S_m(i)}{n} \quad (2.10)$$

where i represents the i th measurement point for an optical metrology device, n is the total number of measurements for the optical metrology device.

Another exemplary termination criterion is a confidence interval cutoff value for optimization parameters. Optimization parameters and confidence intervals are explained in greater detail below. Associated with a profile model is a set of geometric parameters. Optimization parameters are derived from the geometric parameters of the profile model. The process of deriving the optimization parameters from the geometric parameters will also be discussed in detail with regard to FIG. 4. Confidence interval is a range of values of the optimization parameter within which the actual value is expected to fall with a specified probability. As an illustration, a 3-sigma confidence interval of an optimization parameter x1 of 20 nm means there is a 99.7% probability that the actual value of x1 is within + or −20 nm. The confidence interval amount may be set to the amount of change from the nominal value of an optimization parameter where the change in the diffraction signals is greater than a preset value. The preset value may be a value for system noise level or artificial noise level, typically expressed in nanometers. For example, a confidence interval cutoff of 2.0 nm for the middle critical dimension, "CD," of a structure and 2.5 nm for the bottom CD parameter may be specified. The selection of the profile model would continue until the confidence interval cutoff for both the middle and bottom CD's are met.

In step 320, one or more criteria for selection of profile model parameters are determined. Profile selection criteria may include a specific correlation coefficient or sensitivity of a profile parameter. For example, a cutoff of 0.99 correlation may be used to select parameters. Alternatively, a specific change in the signal (ΔS) may be required for each incremental change of the profile parameter (ΔP), where ΔS/ΔP is a measure of the sensitivity of the parameter. The parameter selection criteria will be discussed in more detail in FIG. 5.

Still referring to FIG. 2, in step 330, the characterization of the wafer structure is obtained. An image of the structure from a referencing metrology instrument, such as a cross section-SEM or X-SEM image may be used as a basis for characterizing the profile of the structure. For example, indication of top-rounding, undercutting, T-topping, footing, notching, concavity, convexity, and similar characterization of the structure may be obtained. Wafer fabrication process design data may also be used. Information about the nominal CD and height together with structure image data may be used to characterize the structure profile. For a description of the steps involved in one exemplary process of obtaining characterization of the wafer structure, refer to the description of FIG. 3.

Figure 9A:
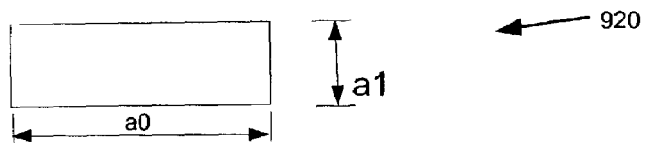
FIG. 9A is an exemplary geometric shape utilized for building a model of the profile of a wafer structure.
Figure 9B:
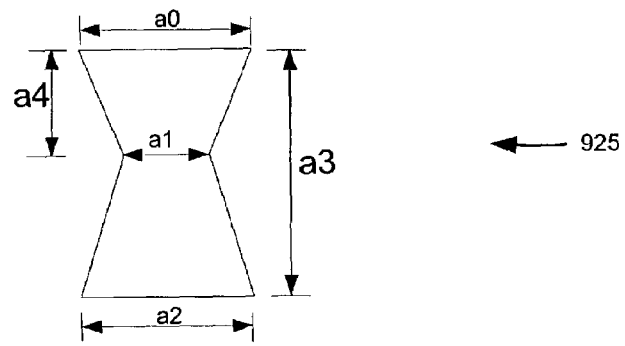
FIG. 9B is an exemplary combination of geometric shapes utilized for building a model of the profile of a wafer structure.

In step 340, the structure characterization is converted into a profile model. A profile model may be a simple rectangle with two parameters designating the height and width of the rectangle. In FIG. 9A, a rectangular shape 920 is shown with two parameters, a0 and a1 representing the width and height respectively. Another model for a profile may be a trapezoid, having three parameters representing for instance the bottom CD, the top CD, and the height. FIG. 9B represents a model with two trapezoids 925, one on top of the other. The two-trapezoid profile model 925 could be described using five parameters, a0 representing the top CD of the top trapezoid, a1 representing the common CD of the top and bottom trapezoids, a2 representing the bottom CD of the bottom trapezoid, a3 representing the total thickness of the top and bottom trapezoids, and a4 representing the thickness of the top trapezoid. A more complex profile model is shown in FIG. 9C with two rectangular blocks, 942 and 944, representing two different films; a trapezoid 940 that represents the bottom of the patterned structure having a footing, two rectangular blocks, 938 and 936, made of a different material, a thin rectangular block 934 representing a notch in the structure, and top trapezoid 932 representing some level of rounding in the top of the structure.

Figure 9C:
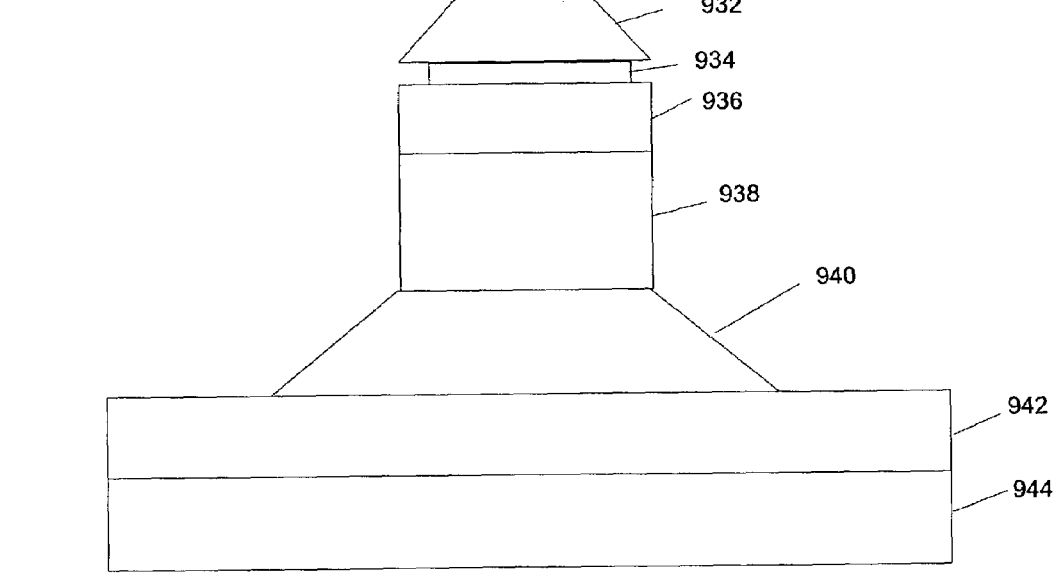
FIG. 9C is an exemplary composite structure using a combination of geometric shapes as a model of the profile of a wafer structure.

As can be seen in FIG. 9C, a profile model may comprise many different geometric shapes in order to get a good approximation of the actual profile of the structure. In general, the more complex the model, the more parameters needed to represent the model. More parameters increase the complexity and length of time to perform the optical metrology simulation of the structure. For a description of simulation of diffraction signals off a hypothetical structure, refer to co-pending U.S. patent application Ser. No. 09/770,997, entitled "Caching of Intra-layer Calculations for Rapid Rigorous Couple-Wave Analyses", by Niu et al., filed on Jan. 25, 2001, incorporated in its entirety herein by reference. As will be described in FIG. 5, for a given profile model, the number of parameters may be optimized in order to select the least number of parameters that still meet the termination criteria.

In step 350 of FIG. 2, the profile model optimization parameters are selected based on one or more selection criteria. As will be discussed in more detail in FIG. 5, the selection of an optimization parameter is based on correlation with other parameters, sensitivity of the simulated signal to a change of the optimization parameter, confidence interval of parameter change that can be detected, and other considerations. Stated another way, and as an example of an exclusion rule, an optimization parameter A may be excluded if parameter A is highly correlated to another parameter B and the simulated signal is insensitive to changes in parameter A.

In step 360, the simulation calculation is optimized by balancing the speed of simulation computations with the accuracy of the computed signal. For example, variables such as number or range of diffraction wavelengths used and the number of diffraction orders considered are optimized to yield the least number of simulation variables and the highest accuracy of the computed signal.

In step 370, a test is performed to see if the termination criteria are met. For example, if one of the termination criteria is a cost function value of less than or equal to 2.50, then the cost function value of a simulated signal using the selected parameters of the selected model is compared to a corresponding measured signal. If the cost function value is 2.20, then this criterion is met. Additionally, a second termination criterion may be a GOF of 0.9990 or greater. Referring to FIG. 11B, the graph 982 of reflectance on the Y-axis as a function of wavelength on the X-axis, measured reflectance curve 984 is compared to simulated reflectance curve 986, the simulation using a double trapezoid profile as illustrated in FIG. 11A. Using the GOF formula, the calculated GOF is 0.9994 as shown in FIG. 11C. However, in the same table 988 in FIG. 11C, the highest 3-sigma confidence interval for optimization parameters is 17.92 nm for x1. As noted above, the confidence interval is a range of values of the optimization parameter within which the actual value is expected to fall with a specified probability. As an illustration, a 3-sigma confidence interval of an optimization parameter x1 of 20 nm means there is a 99.7% probability that the actual value of x1 is within + or −20 nm.

Referring now to FIG. 10B, the graph 960 of reflectance on the Y-axis as a function of wavelength on the X-axis, measured reflectance curve 962 is compared to simulated reflectance curve 964, the simulation using a single trapezoid profile as illustrated in FIG. 10A. Using the GOF formula, the calculated GOF is 0.9990 as shown in FIG. 10C. Note that in table 965 of FIG. 11C, the highest 3-sigma confidence interval for the optimization parameters is 1.99 nm for x0. As explained in more detail below, the lower 3-sigma confidence interval of the single trapezoid model of FIG. 10A compared to the two trapezoid model of FIG. 11A means that the single trapezoid model of FIG. 10A will be selected, given that the GOF criterion of 0.9990 is also met.

Referring now to FIG. 2, when the termination criteria are not met, processing proceeds to step 375, where the parameter selection criteria and/or the profile model is adjusted, and steps 350, 360, and 370 are iterated. Examples of changes to parameter selection criteria may be an adjustment of the correlation cutoff for selecting or excluding a parameter. Alternatively, a sensitivity cutoff, expressed as sum-squared-error values as an example, may be adjusted. An example of a profile model adjustment is using three trapezoids instead of two trapezoids to represent the structure profile or using one trapezoid instead of two trapezoids to model the patterned area of the structure. In one instance, the profile model may be revised to include more or different geometric shapes to get closer to the optical microscopy image of the structure. In another instance, the profile model may be made simpler, such as using only one trapezoid instead of several trapezoids.

In one example, a list of recommended actions to meet the termination criteria may be generated as described below with respect to FIG. 18. The recommended actions may be selected based on experience, intuition, and the like, which may reduce different paths and different results by different users when creating profile models and libraries. Further, the recommended actions may be selected automatically, manually, or a combination of both to reduce the iterations of adjustments and/or standardize the results for different users of different skills and experiences.

In step 380, when the termination criteria are met, the profile model, the selected profile parameters, the parameter selection criteria, the termination criteria, and identification data regarding the fabrication, wafer site, and metrology device may be saved in a data store.

The results of model and parameter selection may be utilized in several ways. For example, in 390, a library of simulated diffraction signals and associated profile data is created using the ranges and resolutions of the selected parameters of the selected model. For a description of the process for creating a library using ranges and resolutions of parameters, refer to co-pending U.S. patent application Ser. No. 09/727,530 entitled "System and Method for Real-Time Library Generation of Grating Profiles" by Jakatdar, et al., filed on Nov. 28, 2000, and is incorporated in its entirety herein by reference. Alternatively, in step 395, the results of model and parameter selections are displayed. In one embodiment, the values of the critical dimensions, profile shape, and film thickness are made available as soon as the one or more termination criteria are met. In another embodiment, some or all of the data saved in step 390 are displayed. In still another embodiment, in step 398, the results of profile model and parameter selection are utilized for fabrication cluster feed-forward or feed-backward control loops. Details of this aspect are discussed in FIG. 6C.

As noted above, with reference to FIG. 3, an exemplary process of obtaining and processing characterization of the wafer structure will be described in greater detail. It is understood that the process described in the following steps is but one technique of obtaining the characterization of the wafer structure. Other techniques may include structure characterization obtained from an integrated circuit fabrication process or from integrated circuit device simulation software.

Figure 3:
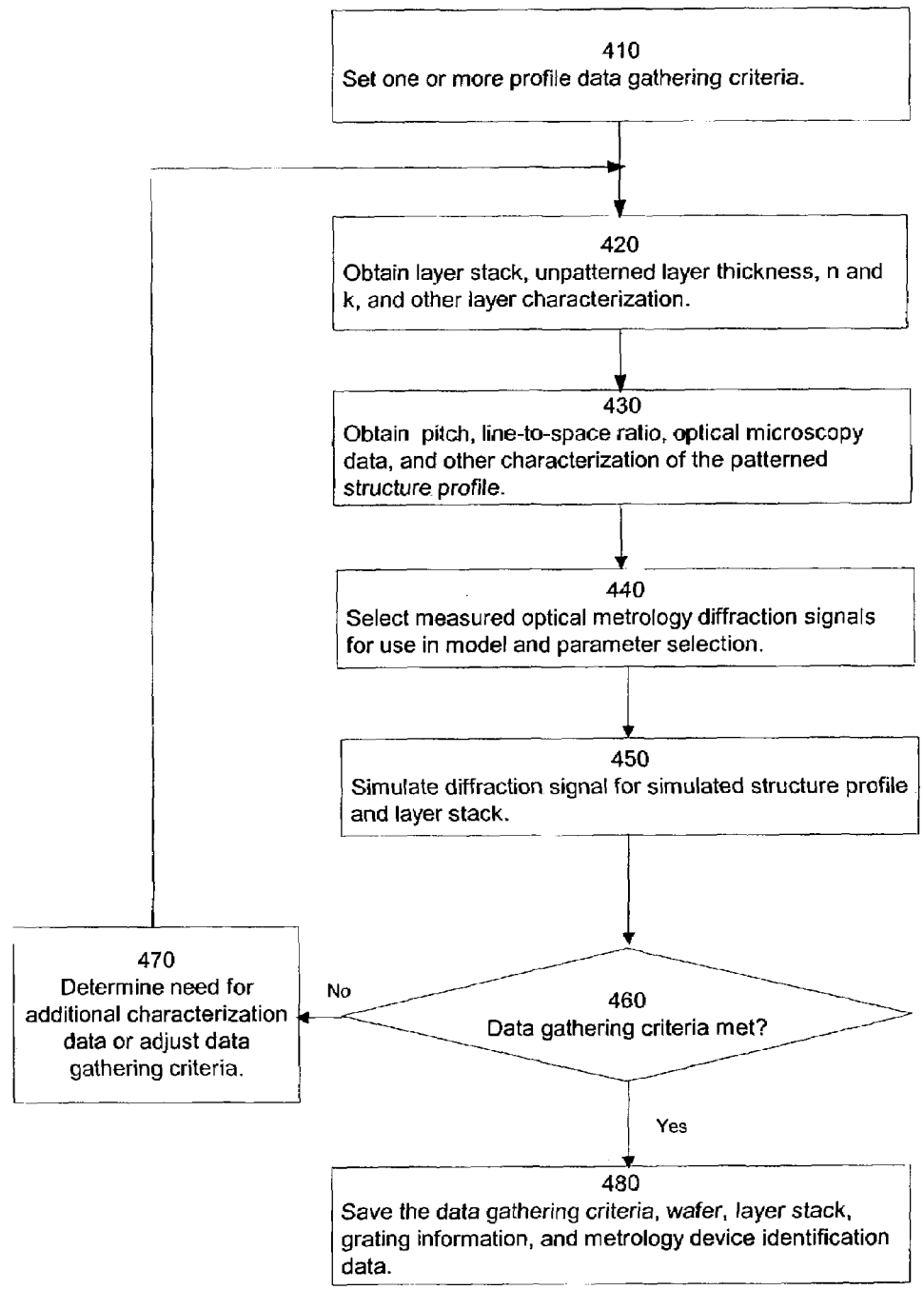
FIG. 3 is an exemplary flowchart for processing characterization of the wafer structure.

Referring to FIG. 3, in step 410, one or more data gathering criteria is set. A data-gathering criterion is used to test whether sufficient data about the structure is available to perform the model and parameter selection. Examples of data gathering criterion may include a cost function value or GOF similar to the termination criteria used in model and parameter selection. However, the cost function value or GOF may be different, typically lower, from those specified for the termination criteria. Other data gathering criteria may include a range of acceptable variation of measured diffraction signals, such as 3-sigma width of measured diffraction signals for the same site in the wafer. For example, if the measured diffraction signals for the same site in a wafer have large standard deviations, then additional diffraction signal measurements of the wafer structure may be needed. Alternatively, the data gathering criteria may be a comparison of the structure profile derived from simulations to an X-SEM image.

Still referring to FIG. 3, in step 420, characterization about the layer stack, unpatterned layer thickness, index of refraction index "n," extinction coefficient "k," and other layer properties are obtained. Characterization includes the type of material used in each layer. In step 430, the pitch of the patterned structure, line-to-space ratio, optical characteristics of the patterned structure, and other characterization of the patterned structure profile are obtained. Other characterization of the patterned structure profile includes data about top rounding, undercut, footing, notching, or other expected anomalies in the profile.

In step 440, measured optical metrology diffraction signals are selected from the input measured diffraction signals. The type and amount of data may vary according to whether an ellipsometer, reflectometer, or other scatterometric device is used, and depending on the specific model and manufacturer of the device. Selection of measured diffraction signals may include several steps designed to test a small number of representative diffraction signals using selection techniques such as clustering, correlation, and the like. The measured diffraction signals are categorized into groups using one or more of the selection techniques listed above. For a description of clustering in optical metrology, refer to co-pending U.S. patent application Ser. No. 09/737,705 entitled "System and Method for Grating Profile Classification" by Doddi, et al., filed on Dec. 14, 2000, incorporated in its entirety herein by reference. Representatives of each cluster or group of highly correlated measured diffraction signal are identified and selected for use in the model and parameter selection processing.

In step 450, the signal off a structure is simulated utilizing the layer stack and structure profile developed from the characterization of the profile. For a description of simulation of diffraction signals off a hypothetical structure, refer to co-pending U.S. patent application Ser. No. 09/770,997, entitled "Caching of Intra-layer Calculations for Rapid Rigorous Couple-Wave Analyses", by Niu et al., filed on Jan. 25, 2001, incorporated in its entirety herein by reference.

In step 460 of FIG. 3, a test is performed to see if the one or more data gathering criteria are met. For example, if the GOF between the simulated signal and the measured diffraction is 0.950 and a data gathering criterion is a GOF of 0.950 or lower, then the data gathering criterion is met. In another example, the data-gathering criterion is a simulated thickness of each layer of the stack being the same or within a given percent of the characterization data provided by the user. For example, if the thickness of a layer of the stack is given as 100 nm and the simulated thickness for that layer is 102 nm, and one data gathering criterion is a variance of 2 percent or less on layer thickness, then the data gathering criterion is met.

Still referring to FIG. 3, in step 480, the data gathering criteria, wafer and structure characterization, and metrology device identification data are saved when the data gathering criteria are met. If the data gathering criteria are not met additional characterization data is obtained or the data gathering criteria are adjusted in step 470. For example, if a data-gathering criterion is a cost function value of the simulated signal and measured signal of 3.50 or better, and the computed cost function value is 7.00, then the data gathering criterion is not met. A basic characterization data may be off. For example, if the pitch of the structure is specified incorrectly or the profile characterization is grossly incorrect, the cost function value could be very high. A review of the characterization data and accuracy of input of these characterizations into the system may be used to identify the cause of the problem. Alternatively, the data gathering criteria may be adjusted if found to be set incorrectly.

Figure 8:
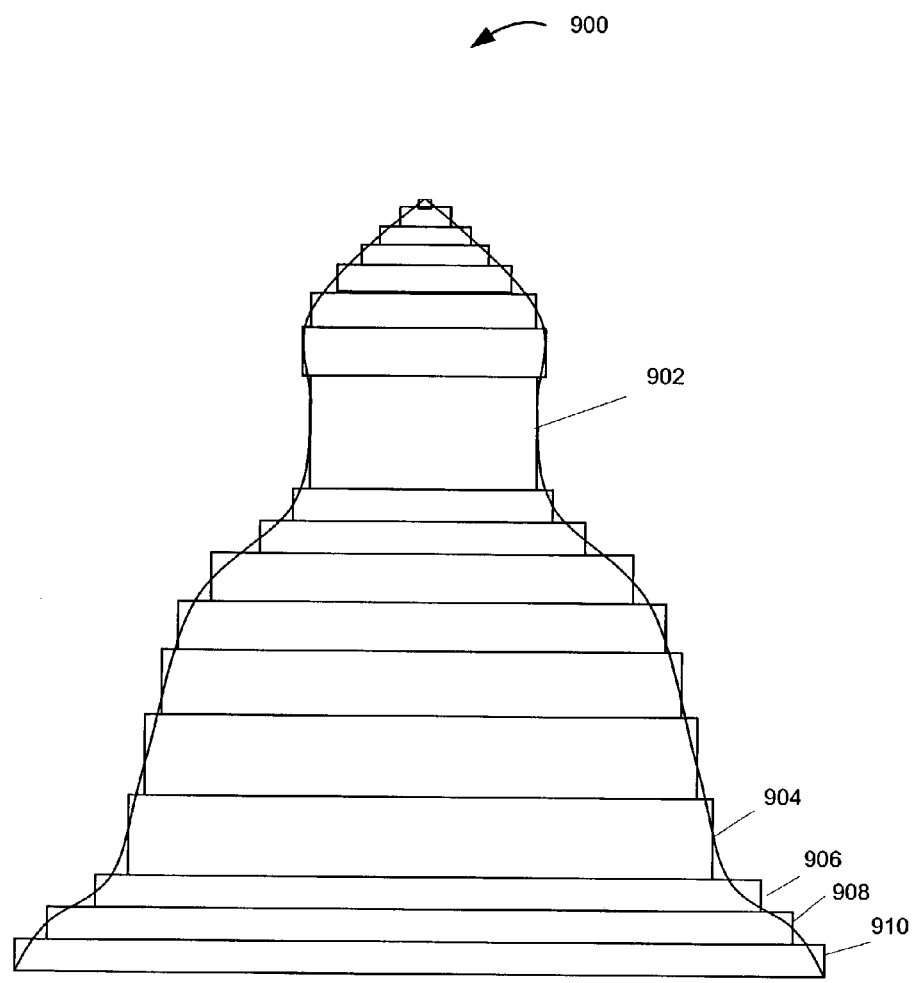
FIG. 8 is an exemplary architectural diagram of a geometric model of the profile of a wafer structure.

As noted above, the description of FIG. 4 provides further detail of an exemplary process for converting the characterization of the wafer structure into a model and associated parameters. In step 510, the types of geometric shapes for each material of the stack are determined. For example, where there is only one material in a stack, one geometric shape may be chosen to represent the entire profile model. In FIG. 8, assuming structure 900 is formed of one material, a set of rectangular shapes of varying dimensions (e.g., rectangular shapes 902, 904, 906, 908, and 910) is used to represent the profile model of structure 900. In FIG. 9A, for an unpatterned film, a rectangular shape is used, whereas in FIG. 9B, two trapezoidal shapes are used. The profile in FIG. 9C utilizes rectangular and trapezoidal shapes.

Figure 4:
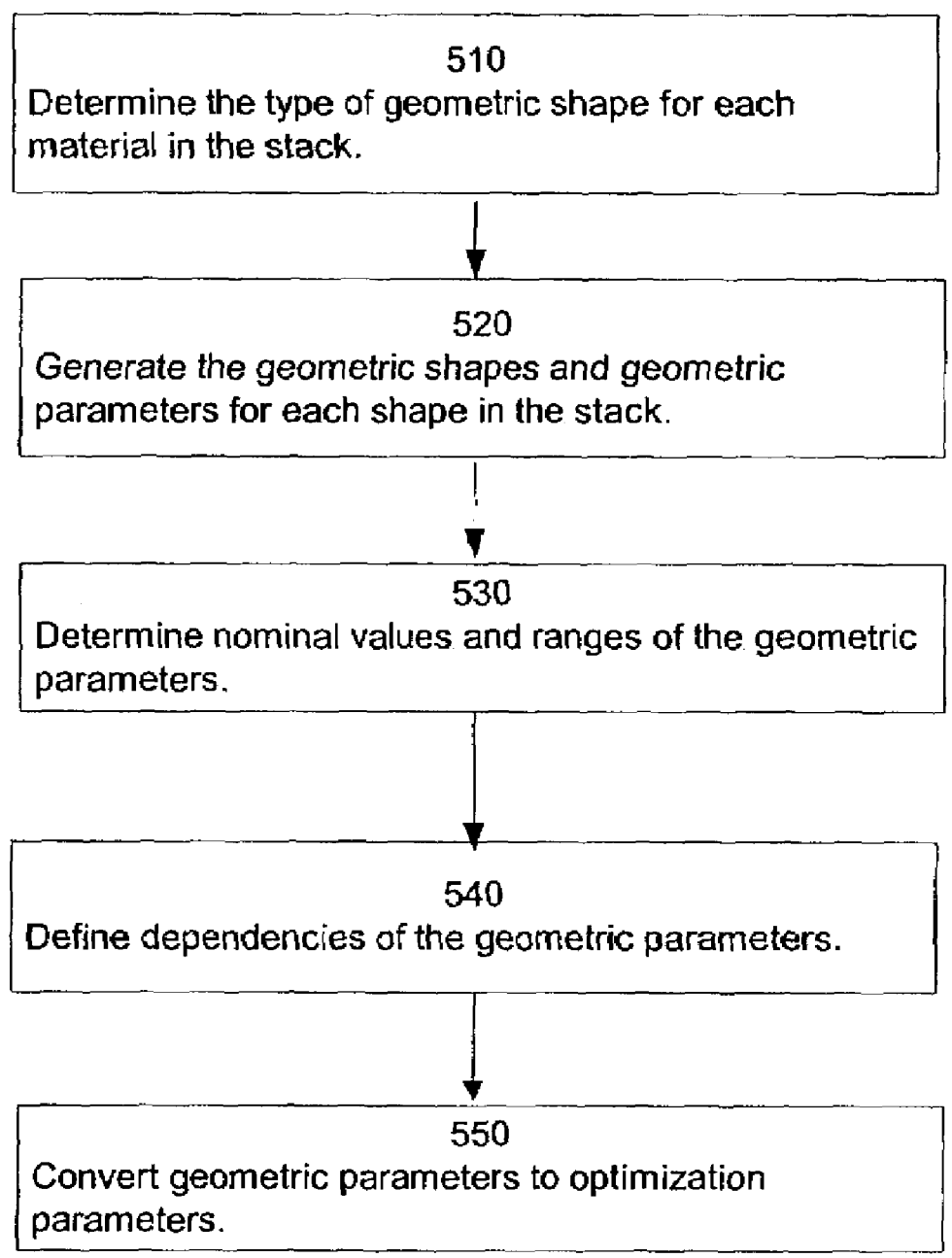
FIG. 4 is an exemplary flowchart for converting characterization of the wafer structure into a model and associated parameters.

With reference to FIG. 4, in step 520, the geometric shapes and parameters of the stack of the structure are generated. For example, if the first layer in an unpatterned stack is represented by the rectangular shape 920 in FIG. 9A, then the geometric parameter is the thickness of the first layer, a1, since the width for an unpatterned layer can generally be assumed to be infinite for diffraction simulation purposes.

If the geometric shape for a layer is a trapezoid, three geometric parameters can be used, namely, the top width, the bottom width, and height of the trapezoid. If a double-trapezoid 925 is used as in FIG. 9B, then five geometric parameters can be used, namely, the top width of the top trapezoid a0, the bottom width of the top trapezoid a1, which is also the top width of the bottom trapezoid, the bottom width of the bottom trapezoid a2, the total thickness of the structure model a3, and the thickness of the top trapezoid a4.

The profile model 930 of FIG. 9C depicts a complex profile model where the model includes rectangular shapes 936, 938, 942, and 944, a rectangular shape to illustrate notching in the structure 934, and trapezoidal shapes 932 and 940 to illustrate a top rounding of the structure and a bottom footing of the structure respectively. The geometric parameters are the sum of individual geometric parameters of the individual geometric shapes. For the complex profile model 930 of FIG. 9C, the number of geometric parameters is high. Typically, the more geometric shapes, the higher the number of geometric parameters. Furthermore, the higher number of geometric parameters of a profile model results in a longer simulation process for determining the simulated diffraction signals. As mentioned previously, a longer diffraction simulation process may result in a considerably longer library creation time or regression time.

In step 530 of FIG. 4, the nominal values and ranges of the geometric parameters are obtained. These values and ranges are typically obtained from historical or test data for the fabrication process or recipe. For example, a top width or top CD may have a nominal value of 200 nm and a range of 120 to 280 nm.

In step 540, the dependencies of the geometric parameters are defined. Again, the dependencies of the geometric parameters are based on historical or test results for the particular fabrication process of recipe. For example, in a shallow trench isolation (STI) structure having a silicon nitride cap and a silicon trench, the nitride cap typically determines the CD of the top width of the silicon trench. In this case, the independent geometric parameter is the nitride cap bottom CD. The top CD of the nitride cap and the top width of the silicon trench may be tied to the bottom CD of the nitride cap.

Using the double-trapezoid model 925 of FIG. 9B as an example, the top width a0 of the top trapezoid may be a function of the bottom width a1 of the top trapezoid; a0 may have a linear relation to a1; for example, a0 may be equal to a1 plus a constant or a0 may be equal to a1 multiplied by a fixed number. The relation of a geometric parameter to another geometric parameter may be characterized by a simple linear function, a quadratic function, polynomial function or the like. Dependencies of the geometric parameters of the profile model are defined based on whether a geometric parameter is an independent parameter, has a fixed offset from other parameters, has a variable offset from other parameters, or has a fixed value. For the sake of illustration, consider the double trapezoid of FIG. 9B having five geometric parameters. From design or previous experience with the fabrication recipe, a0 may be known as an independent parameter. Also from previous fabrication data, a1 may be known to have a constant offset from a0 of 10 nm, a2 has a variable offset from a0, a3 is a constant, and a4 is two times a0.

Still referring to FIG. 4, in step 550, the geometric parameters are converted to optimization parameters, x. Reasons for conversion of geometric parameters into optimization parameters include reduction of the search space for regression to determine the optimized simulation diffraction signal (discussed later in FIG. 5). Another reason for conversion of geometric parameters into optimization parameter is reduction of correlation of a parameter to the other parameters.

The result of the conversion is an equation in terms of the optimization parameter $x_i$. For example, the equation for each geometric parameter $a_i$ of the double trapezoid shown in FIG. 9B, having the dependencies described above is as follows:

$a0 = x0$, $a1 = x0 + 10$, $a2 = x0 + x1$, $a3 = 50$ $a4 = 2 \times 0$, where a0, a1, a2, a3, and a4 are the geometric parameters of the profile model as defined above, expressed in nanometers, and x0 and x1 are the optimization parameters of the profile model. Note that the five geometric parameters have been converted into two optimization parameters. It should be noted that more complicated profile models may typically require more geometric parameters and may generally require a corresponding higher number of optimization parameters. It is understood to a person knowledgeable in the art, that other equivalent ways of expressing the dependencies of the geometric parameters to optimization parameters may be used.

Figure 5:
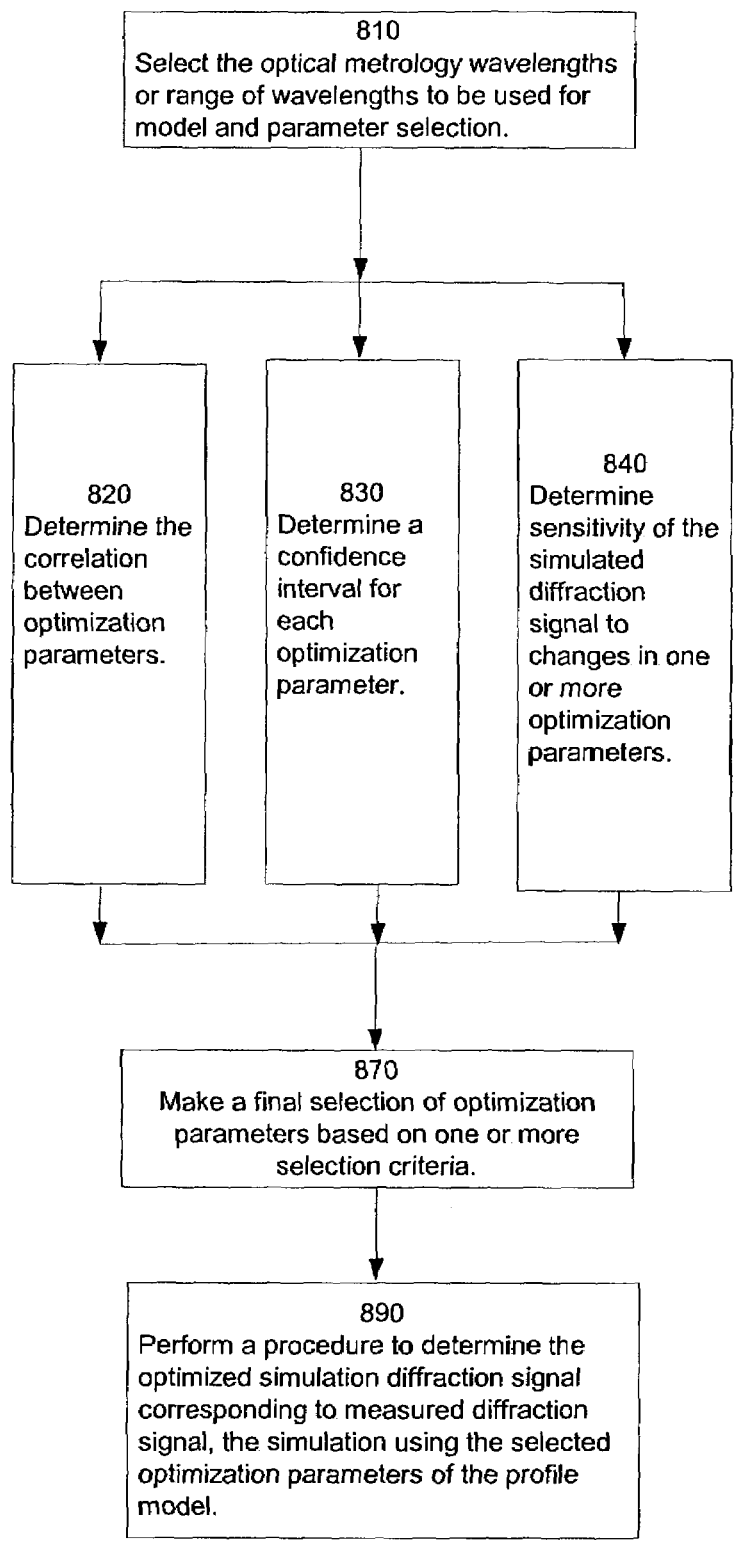
FIG. 5 is an exemplary flowchart for selecting parameters of the model based on one or more selection criteria.

As noted above, the description of FIG. 5 that follows provides more detail regarding the overall flowchart step of selecting parameters of the model based on one or more selection criteria. Referring to FIG. 5, in step 810, the optical metrology wavelengths or range of wavelengths for profile model selection are selected. For a description of the process to select wavelengths, refer to co-pending U.S. patent application Ser. No. 10/162,516, entitled "Selection of Wavelengths for Integrated Circuit Optical Metrology", by Doddi, et al., filed on Jun. 3, 2002, incorporated herein in its entirety by reference. Several tasks may be concurrently or serially performed to provide information as to whether an optimization parameter should be selected or excluded.

In step 820, the correlation between the optimization parameters is determined. Typically, a correlation coefficient, r, between two optimization parameters is calculated using the formula:

$$r = \frac{\sum_i (x_i - \bar{x})(y_i - \bar{y})}{\sqrt{\sum_i (x_i - \bar{x})^2} \sqrt{\sum_i (y_i - \bar{y})^2}} \quad (2.60)$$

where $x_i$ and $y_i$ is a pair of optimization parameters, $\bar{x}$ is the mean of $x_i$'s and $\bar{y}$ is the mean of $y_i$'s. The value of r lies between −1 and +1 inclusive. A correlation coefficient value of +1 can correspond to complete positive correlation and a value of −1 can correspond to complete negative correlation. A value of r close to zero can correspond to the x and y optimization parameters not being correlated.

Figure 12A:
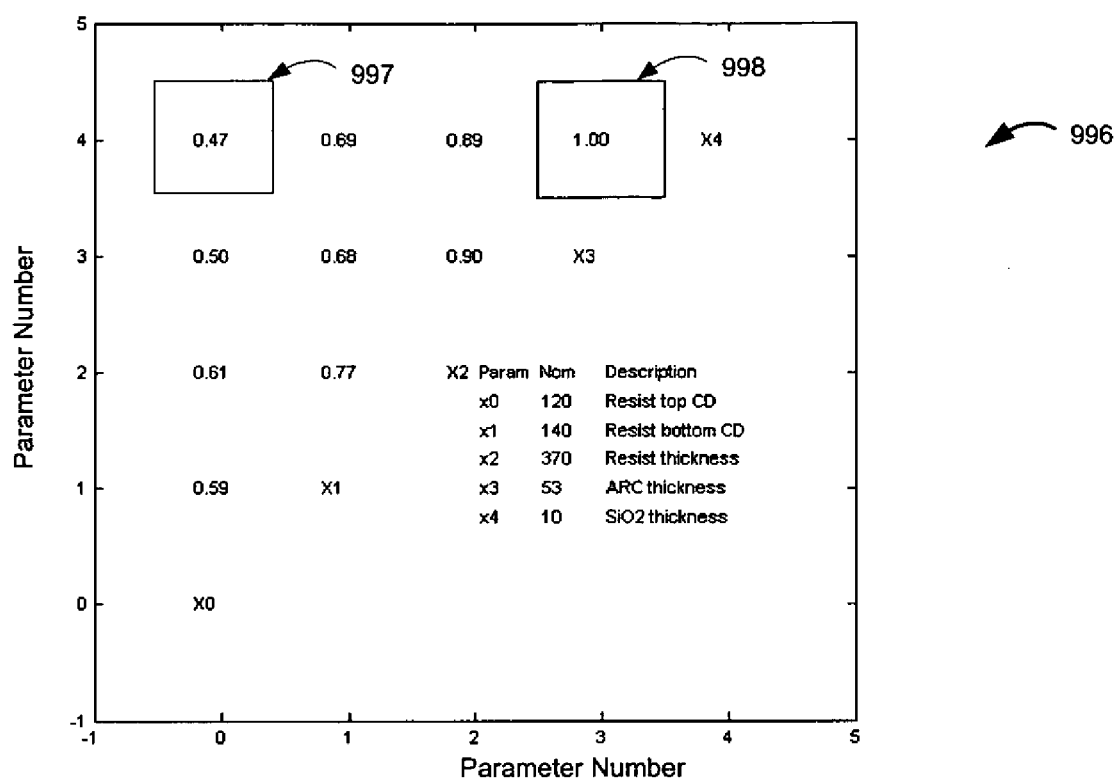
FIG. 12A is an exemplary table of correlation coefficients of parameters of a wafer structure profile model.
Figure 12B:
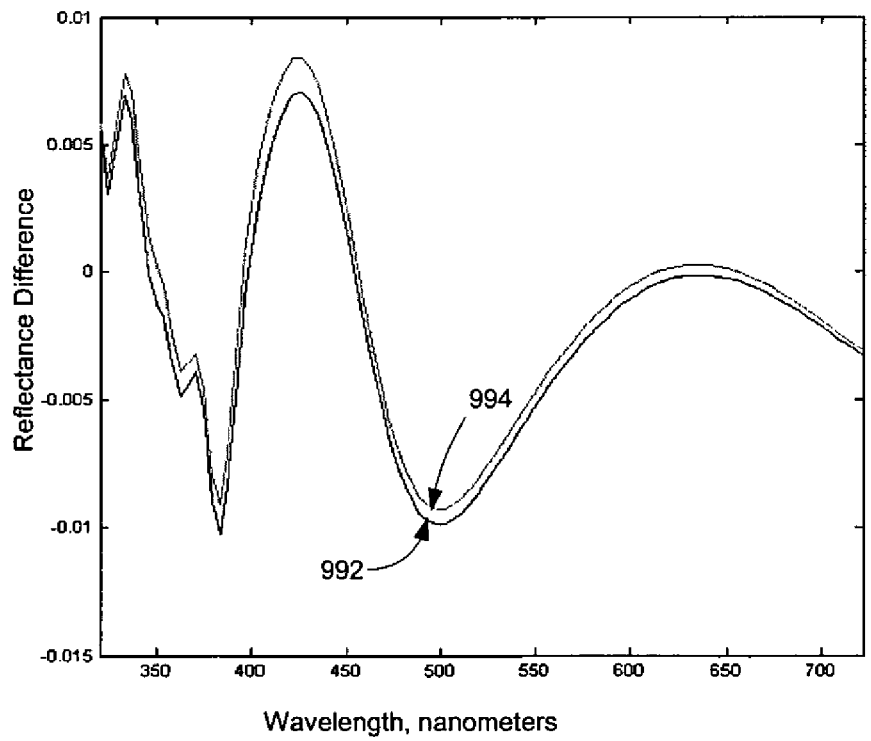
FIG. 12B is an exemplary reflectance difference graph of two parameters of a profile model that have complete correlation.

Referring to FIG. 12A, the table of correlation coefficients 996 shows five optimization parameters, namely, x0 representing the resist top CD, x1 representing the resist bottom CD, x2 representing the resist thickness, x3 representing the anti-reflective coating thickness, and x4 representing the silicon dioxide thickness. The correlation coefficient table 996 is configured such that the Y-axis and the X-axis have the parameter numbers shown. An intersection or cell represents the correlation coefficient of a parameter matched to a different parameter. For example, at the intersection of parameter x0 and x4, cell 997, the correlation coefficient is 0.47. The correlation coefficient is calculated by substituting input measured values of x0 for $x_i$ and x4 for $y_i$ in equation 2.60 above. The low correlation coefficient value means that parameter x0 and x4 are not highly correlated. In contrast, at the intersection of parameter x3 and x4, cell 998, the correlation coefficient is 1.00, meaning complete positive correlation between x3 and x4. As can be seen in FIG. 12B, the reflectance difference graph versus wavelength of parameter x3, graph 992, has complete positive correlation to the reflectance difference graph versus wavelength of parameter x4, graph 994. In terms of optimization parameter selection, only one of parameter x3 and x4 need to be included, since the variation of the diffraction signals caused by either x3 or x4 can be determined from the variation of the other.

In step 830 of FIG. 5, the confidence interval of each optimization parameter is determined. As previously noted, the confidence interval may be set to the amount of change from the nominal value of an optimization parameter where the change in the diffraction signals is greater than the noise level. The noise in the diffraction signals may be due to system noise, for example, noise from the measurement devices, or the noise may be simulated. The confidence interval is generally expressed as a multiple of the standard deviation sigma, σ, of the optimization parameter. The standard deviation for an optimization parameter is calculated from measured values of the optimization parameter, using the formula:

$$\sigma = \sqrt{(([1/(N-1)]) * (x_i - x_{av})^2)} \quad (2.70)$$

where N is the number of measurements, $x_i$ is the i th value of the optimization parameter x, and $x_{av}$ is the average value of the optimization parameter x.

The confidence interval is typically calculated from a given set of sample input data representing actual measurements off the wafer structure. The confidence interval may also be calculated using simulated random noise introduced in the measurement data for the optimization parameter.

With reference to FIG. 10A, the structure profile model 950 using a single trapezoid 951 on top of a rectangular shape 953 representing a structure with a single layer of underlying film has four optimization parameters, namely, x0 representing the top CD of the structure, x1 representing the bottom CD of the structure, x2 representing the width of the structure, and x3 representing the width of the underlying film. With reference to FIG. 10C, a table 965 is shown with the 3-sigma confidence interval for the four-optimization parameters. For example, optimization parameter x0 has a confidence interval of 1.99 nm, meaning that measurement of x0 has a probability of 99.7% being visible or sensitive to within 1.99 nm. Alternatively, if the change in x0 is less than 1.99 nm, then there is a 99.7% probability the change would not show in the signal. Similarly, x1 has a 3-sigma confidence interval of 1.95 nm, and so on. Note that parameter x3 has a 3-sigma confidence interval of 0.30, meaning that parameter x3 is sensitive to changes greater than 0.30 nm.

Assuming that the same structure as discussed in FIG. 10A was modeled using two trapezoids 972 on top of a rectangular shape 974 as in the profile model 970 in FIG. 11A. The double-trapezoid profile model 970 has six optimization parameters, namely, x0 representing the top CD of the top trapezoid 976, x1 representing the middle CD of the bottom trapezoid 978, x2 representing the bottom CD of the bottom trapezoid 978, x3 representing the width of the double trapezoid 972, x4 representing the ratio at the inflection point, equal to h1, the width of the top trapezoid 976, over the width of the double trapezoid 972, and x5 representing the width of the underlying film. With reference to FIG. 11C, a table 988 is shown with the 3-sigma confidence interval for the six-optimization parameters. For example, optimization parameter x0 has a confidence interval of 6.81 nm, meaning that measurement of x0 has a probability of 99.7% being visible or sensitive to within 6.81 nm. Alternatively, if the change in x0 is less than 6.81 nm, there is 99.7% probability the change in x0 would not show in the signal. As will be discussed in a later step 870, the entire collection of data calculated for each optimization parameter can be integrated into a decision-making step as to whether to include or exclude an optimization parameter.

In step 840 of FIG. 5, the sensitivity of the simulated signal to changes in one or more optimization parameters is determined. Typically, this determination is done by changing one optimization parameter by a small amount and keeping the other optimization parameters constant. For example, in the profile model in FIG. 10A using one trapezoid, the sensitivity of parameter x0 may be tested by adding one nanometer to the nominal value while keeping x1, x2, and x3 at nominal value and simulating the signal. If there is no noticeable change in the signal matrix or graph of (x0 at nominal plus 1 nm), then x0 has low sensitivity. The other optimization parameters can similarly be changed while holding the rest constant in order to test the sensitivity of each optimization parameter.

The sensitivity of an optimization parameter may be quantitatively expressed by calculating the sum-square-error (SSE) of the changed signal compared to the signal using nominal values. The SSE formula is as follows:

$$SSE = \sum_{i=1}^{n} (S_o(i) - S_1(i))^2 \quad (3.00)$$

where i is the signal simulation point, typically at a preset wavelength, n is the number of signal simulation points, $S_o$ is the simulated signal value using nominal values of optimization parameters, $S_1$ is the simulated signal value using nominal plus change in one of the optimization parameters.

In step 870 of FIG. 5, the final selection of optimization parameters is made based on one or more selection criteria. For example, a parameter selection criterion may be a cutoff point in the correlation coefficient. Parameters with a correlation coefficient lower than 0.50 with respect to all other parameters may be selected. Alternatively, a pair of parameters with a correlation coefficient of 0.98 may be further tested as to sensitivity in order to determine which parameter is selected, or which parameter is excluded. An SSE threshold may be used to select optimization parameters. For example, an SSE threshold of 0.01 may be used to filter optimization parameters that are relatively insensitive to changes of the parameter. A certain cutoff for the 3-sigma confidence interval may also be used to screen out optimization parameters that do not meet these criteria or to flag profile models that do not yield the proper sensitivity of key parameters critical to the IC design. A combination of the above criteria may be used. It is understood that other equivalent criteria known to one knowledgeable in the art may be used. If an optimization parameter is not selected, then the optimization parameter is set to a fixed value, the fixed value determined from fabrication data or previous experience with the recipe.

In step 890, a procedure is performed to determine the optimized simulation diffraction signal to the measured signal using the selected optimization parameters of the selected profile model. One embodiment uses a regression technique to get to the optimized simulation signal. One or more types of regression engines may be used.

Figure 7:
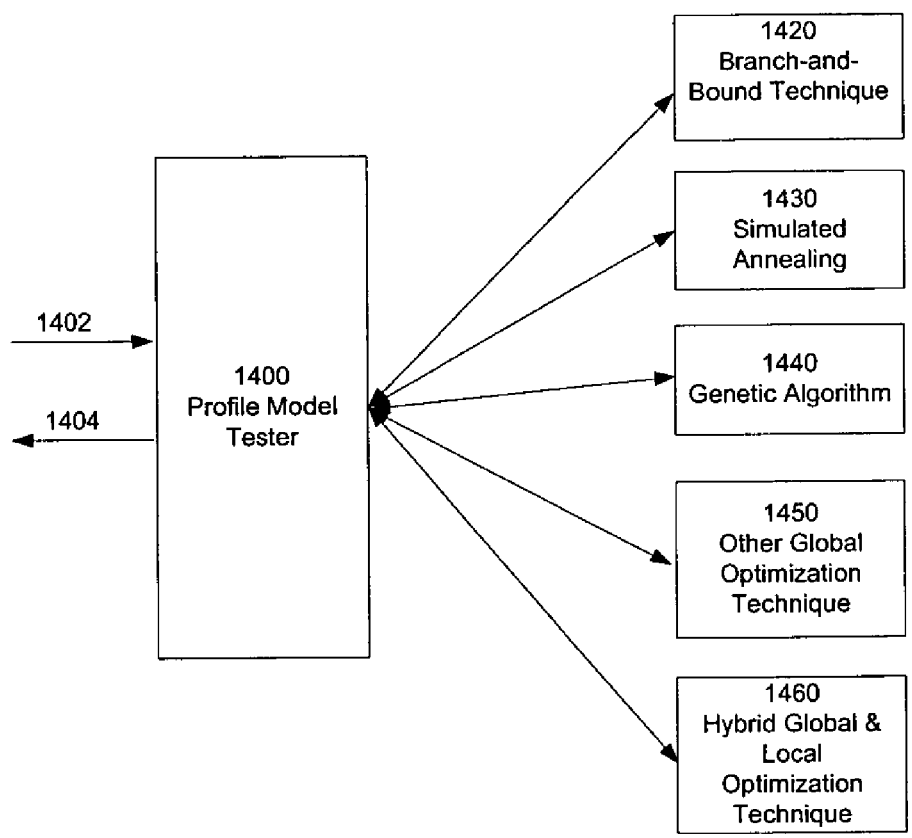
FIG. 7 is an architectural diagram depicting the use of optimization engines in an exemplary embodiment.

With reference to FIG. 7, an exemplary profile model tester 1400 receives the selected profile model, selected optimization parameters, and measured diffraction signals 1402. The profile model tester 1400 processes the input data and activates one or more optimization engines, such as branch-and-bound technique 1420, simulated annealing 1430, genetic algorithm 1440, other global optimization technique 1450, or hybrid global and local optimization technique 1460. The optimization engines arrive at a global minimum of the difference between the simulated signal and the measured signal. The simulated signal corresponding to the global minimum in turn corresponds to a set of values of the optimization parameters of the selected profile model, which the profile model tester 1400 creates as an output 1404.

Figure 6A:
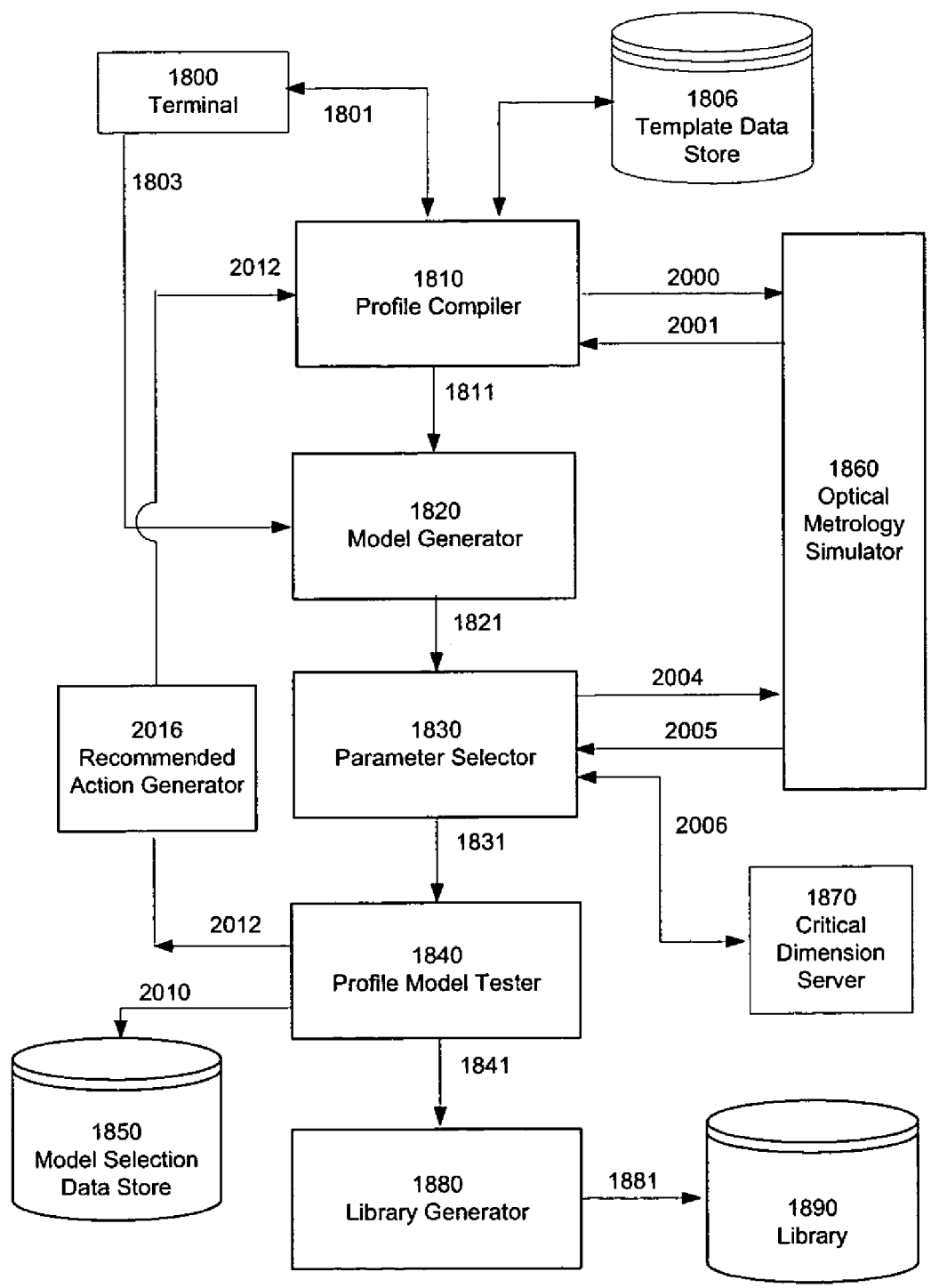
FIG. 6A is an architectural diagram depicting a system for model and parameter selection in an exemplary embodiment.

FIG. 6A is an architectural diagram depicting a system for model and parameter selection in one exemplary embodiment. In the present embodiment, a terminal 1800 is used to enter wafer fabrication process design data including the characteristic of process and modeling attributes such as the stack, n and k values, nominal profile parameter values and ranges, width nominal values and ranges, measured diffracted signals off several sites in the wafer, and structure image data to characterize the structure profile. In one example, as described with regard to FIG. 20, the input data may be transmitted to a template selector and used to select a suitable template based on the particular characteristics of process and modeling attributes that are known. Choices of termination and optimization parameter selection criteria may also be entered on the terminal 1800 and transmitted as input 1801 to a profile compiler 1810 and input 1803 to a model generator 1820. The profile compiler 1810 edits the input data 1801 and invokes an optical metrology simulator 1860 to simulate the signal with the specified nominal values of the geometric parameters of the profile model 2000. The optical metrology simulator 1860 transmits the simulated diffraction signal 2001 to the profile compiler 1810. As mentioned above, a description of simulation of diffraction signals off a hypothetical structure, refer to co-pending U.S. patent application Ser. No. 09/770,997, entitled "Caching of Intra-layer Calculations for Rapid Rigorous Couple-Wave Analyses", by Niu et al., filed on Jan. 25, 2001, incorporated in its entirety herein by reference. The profile compiler 1810 performs a comparison of the simulated signal 2001 to the measured signal from the input 1801, sending data to terminal 1800 regarding the quality and adequacy of the input data 1801. The profile compiler 1810 may also process adjusted profile model data 2012 from a profile model tester 1840.

Referring to FIG. 6A, the profile compiler 1810 transmits the edited characterization data and measured diffraction signals 1811 to a model generator 1820. The model generator 1820 creates a profile model of the structure comprising geometric shapes. The geometric shapes are expressed in terms of geometric parameters and converted into optimization parameters 1821, which are transmitted to a parameter selector 1830. The parameter selector 1830 uses optimization parameter selection criteria to select which optimization parameters meet the correlation coefficient cutoff, the sensitivity threshold, and/or confidence interval requirements from the customer. The parameter selector 1830 invokes the optical metrology simulator 1860 to perform simulations of diffraction signals with profile parameter data 2004. In turn, the optical metrology simulator 1860 performs simulation of the diffraction signal and transmits simulated diffraction signals 2005 to the parameter selector 1830.

Part of the parameter selector 1830 function is to perform a procedure to determine the optimized simulated signal for each measured signal, invoking one or more optimization engines discussed in FIG. 7. After the optimization process, the optimized profile data comprising profile, CD, and film thickness is transmitted as output 2006 to critical dimension server 1870. The parameter selector 1830 transmits the selected optimization parameters 1831 to the profile model tester 1840, where the termination criteria such as cost function value, GOF, and/or other termination criterion are tested. If the termination criteria are not met, the profile model tester 1840 may be configured to adjust the profile model automatically, for example, by switching from a two-trapezoidal model to a single trapezoidal model or switching from a simple geometric model to one using more geometric shapes to approximate the profile model more closely. The adjusted profile model 2012 is transmitted to the profile compiler 1810.

If the termination criteria are met, the profile model tester 1840 stores the profile model termination criteria, optimization parameter selection criteria, fabrication process, wafer site, optical metrology device identification data, and selected optimization parameters 2010 in a data store 1850. The profile model tester 1840 transmits the optimization parameters 1841 to a library generator 1880, which creates a library 1890 comprising diffraction signals and associated profile data 1881, using the ranges and resolution of the selected optimization parameters. Additionally, if the termination criteria are met, the profile model tester 1840 may generate the list of recommended changes and prompt the user that additional improvements to the approximation of the profile model may be possible.

Figure 6B:
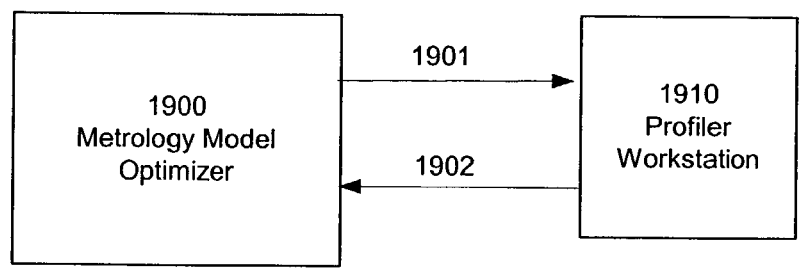
FIG. 6B is an architectural diagram of a metrology model optimizer in an exemplary embodiment.

FIG. 6B is an architectural diagram depicting a system for model and parameter selection in an exemplary embodiment. Metrology model optimizer 1900 receives requests 1902 for critical dimensions, profiles, and film thickness of measured diffraction signals from a profiler workstation 1910. Based on this request 1902 and other input data (not shown) characterizing the subject structure on the wafer, metrology model optimizer 1900 selects a model and parameters in a process similar to that described in FIG. 6A. The metrology model optimizer 1900 produces the requested critical dimensions, profiles, and film thickness associated with a measured diffraction signals and transmits these results 1901 back to the profiler workstation 1910. The profiler workstation 1910 may be located at a remote user site. Access to the metrology model optimizer 1900 may be through a private network, a public network suck as the Internet, and the like.

Figure 6C:
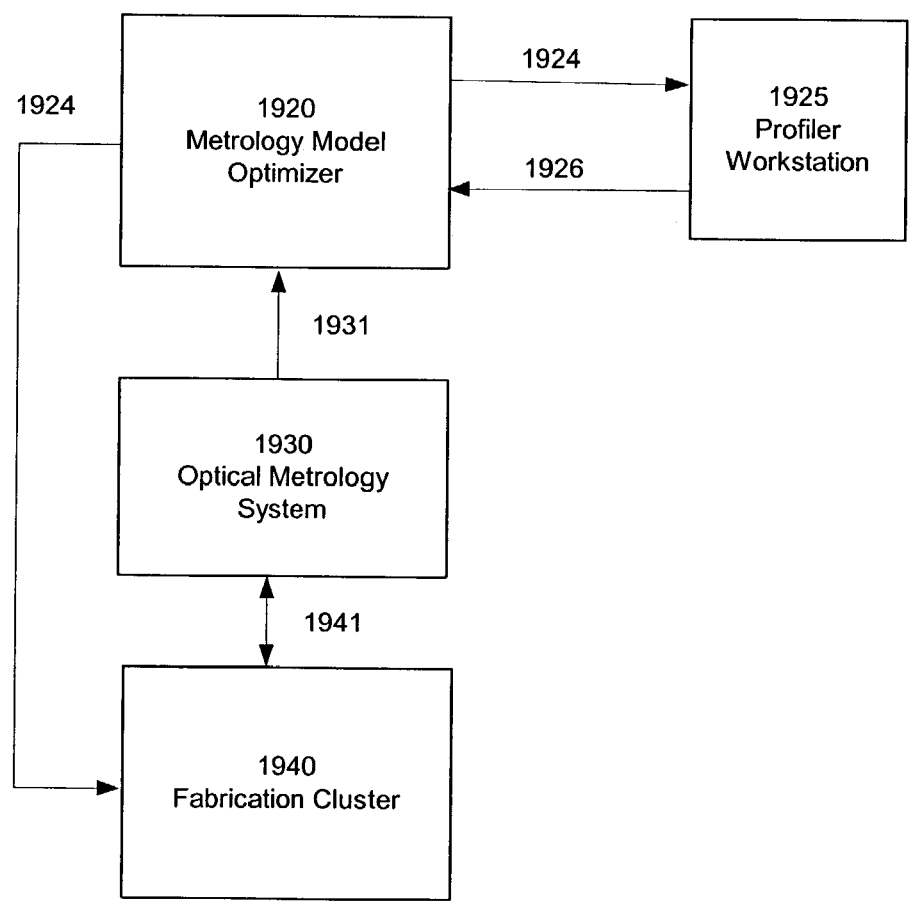
FIG. 6C is an architectural diagram of a metrology model optimizer integrated with a wafer fabrication cluster.

FIG. 6C is an architectural diagram of a metrology model optimizer in an exemplary embodiment. The system configuration is similar to the system in FIG. 6B except that instead of processing request for critical dimension data 1924 exclusively from the profiler workstation 1925, in-line requests 1931 for the same data is transmitted from an optical metrology system 1930. The optical metrology system 1930 is coupled to a fabrication cluster 1940, which may be a clean track unit, lithography machine, an etch machine or a combined lithography-and-etch unit. As a wafer (not shown) completes a fabrication process step, structures on the wafer are measured by the optical metrology system 1930 creating measured diffraction signals 1931 transmitted to the metrology model optimizer 1920. In addition to the critical dimension data 1924 being transmitted to the profiler workstation 1925, the same data is transmitted to the fabrication cluster 1940 for advanced process control use. The critical dimension data 1924 may be used by the fabrication cluster 1940 to adjust process variables of the fabrication process. The profiler workstation 1925 sends requests 1926 for critical dimensions, profiles, and film thickness of measured diffraction signals and other input data (not shown) characterizing the structures on the wafer or location of similar data stored in the metrology model optimizer 1920. The optical metrology system 1930 receives transmitted data 1941 from the fabrication cluster 1940 regarding completion of one or more fabrication processes. After completing the measurements of structures on the wafer, the optical metrology system transmits signals 1941 to the fabrication center 1940 to indicate completion of optical metrology measurements.

FIGS. 13A, 13B, 13C, and 13D are exemplary structure profiles using different profile models. FIG. 13A illustrates a structure modeled with a single trapezoid T1, whereas FIG. 13B illustrates the same structure modeled with two trapezoids T1 and T2. In similar manner, FIG. 13C illustrates the same structure modeled with three trapezoids T1, T2, and T3, whereas FIG. 13D illustrates the same structure modeled with four trapezoids T1, T2, T3, and T4.

As can be seen in FIGS. 13A and 13B, matching of the structure shape to the model is not close in FIG. 13A, but FIG. 13B with two trapezoids shows a dramatic increase in the match between the model and the structure shape. There are some further but minor improvements in the models matching the structure shape as the number of trapezoids used increases to three and four.

FIG. 13E illustrates exemplary graphs of the cost function and GOF of simulated diffraction signals versus the measured signals as a function of the number of geometric shapes used in the profile model. Graph 1000 illustrates how the cost function and GOF varies as the number of trapezoids used in the profile model is increased. As can be seen in the cost function graph 1004, the cost function value of modeling the structure depicted in FIG. 13A with one trapezoid is relatively high at 3.0. The cost function graph 1004, using the left Y-axis, drops dramatically to about 1.5 with two trapezoids, less as the number of trapezoids increases from two to three and from three to four trapezoids. The GOF graph 1002, using the right Y-axis, increases dramatically from a GOF of about 0.920 to 0.97 when the number trapezoids increases from one to two, less as the as the number of trapezoids increases from two to three and from three to four trapezoids. As discussed previously, the profile model selection determines the simplest combination of geometric shapes in the profile model that meets or exceeds the termination criteria, which may be a cost function value and/or a GOF value. As also discussed above, the profile model may be a combination of different types of geometric shapes, where trapezoid is just one possible shape that can be used.

Figure 14:
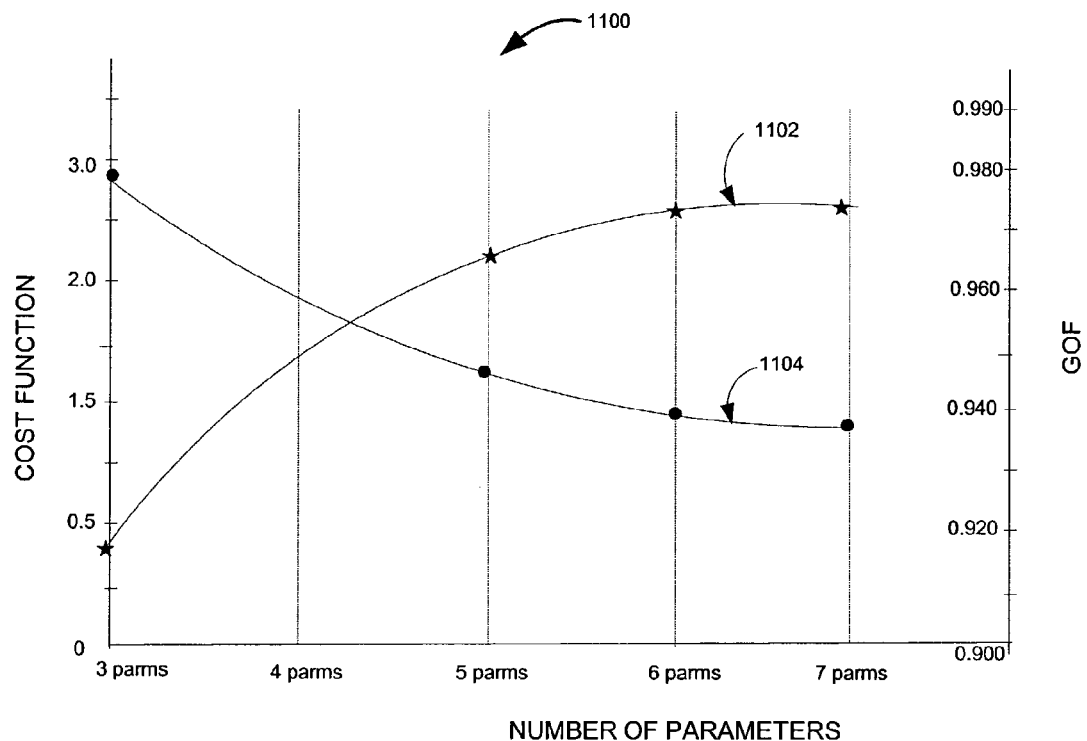
FIG. 14 is an exemplary graph of the cost function and GOF of simulated signal versus the measured signal as a function of the number of parameters used in the profile model.

FIG. 14 is an exemplary graph of the cost function and GOF of simulated diffraction signals versus the measured signals as a function of the number of parameters used in the profile model. Graph 1100 illustrates how the cost function and GOF varies as the number of parameters used in the profile model is increased. As can be seen in the cost function graph 1104, the cost of modeling a hypothetical structure with three parameters is relatively high at 2.9. The cost function graph 1104, using the left Y-axis, drops dramatically to about 1.6 with five parameters, less as the number of parameters increases from five to six and from six to seven parameters. The GOF graph 1102, using the right Y-axis, increases dramatically from a GOF of about 0.915 to 0.965 when the number of parameters increased from three to five, less as the number of parameters increases from five to six and from six to seven parameters.

As discussed previously, the optimization parameter selection selects parameters that are uncorrelated, have high sensitivity, and allows detection of the change in parameter size required by the application. The selected optimization parameters of the profile model are used to simulate the diffraction signals for different profile dimensions, and the simulated diffraction signals are compared to the corresponding measured signals to calculate the cost function and GOF. Once the profile model selected and the selected optimization parameters of the selected profile model provide simulated diffraction signals results that meet or exceed the termination criteria, then the selection process is complete. As discussed above, the regression results such as CD's, film thickness, and profile from the parameter selector 1830 of FIG. 6A may be used by a system user to fine-tune the recipe or fabrication process. Alternatively, the regression results may be used to adjust variables and/or physical controls of the fabrication process. As also noted above, the profile model and optimization parameters selected may be used to create a library of simulated signals and associated profile data.

Figure 15:
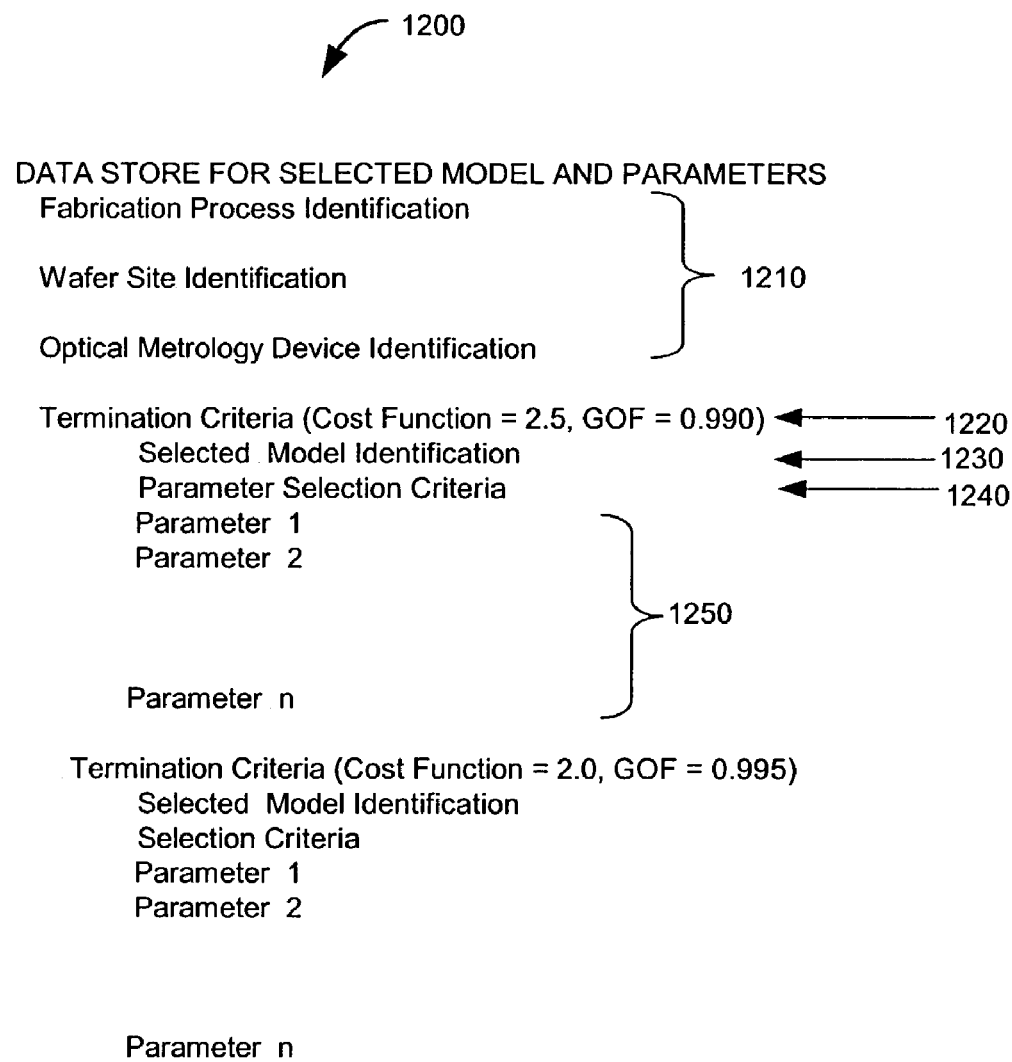
FIG. 15 is an exemplary model and parameter selection data store layout.

FIG. 15 is a storage layout of data store layout in an exemplary embodiment. The data store format 1200 for selected model and parameters includes fabrication process, wafer site, structure, and optical metrology device identification data 1210. The data store format 1200 may include one or more data segments, each data segment comprising the termination criteria 1220, selected model identification 1230 and optimization parameter selection criteria 1240, and selected optimization parameters 1, 2, . . . n, 1250. For example, the model identification may be Shallow Trench Isolation Single Trapezoid Model, termination criteria may include a cost function of 1.5 and GOF of 0.995, optimization parameter selection criteria may be a correlation coefficient of 0.50 and sensitivity of 0.01 SSE, and the selected optimization parameters may be resist top CD, resist bottom CD, resist thickness, anti-reflective coating thickness, and silicon dioxide thickness.

According to another embodiment, a method and system are provided to reduce or eliminate variation between different users in a process for model and parameter selection for optical metrology of wafer structures. Further, the method and system may reduce the iterations to achieve a desired model for library creation and provide an automated and optimized modeling process. In one exemplary method, various parameters of common applications are categorized into templates, such that multiple users may select a specific template to begin a modeling process from a common starting point. In one example, the template includes parameters associated with characterizations of the wafer structure process, such as the recipe including lithography, etching, and the like to produce the structure as well as structure layer materials and the like. The template may further include modeling attributes, such as the optical metrology device, geometric components of the modeling profile, n and k, and other parameters that are associated with the wafer structure and material layers. The characteristics of process and modeling attributes are categorized into templates for different applications based, at least in part, on known models and values including expected parameters and parameter ranges. For example, a specific template (or templates) may be associated with a metal shallow trench isolation "STI," process and structure. The template for the metal STI application may include preset parameter values and ranges based on, for example, prior knowledge and/or experience in creating and testing profile models to meet termination criteria.

A profile model may be generated based on the parameters of the template. A calculated signal based on the parameters of the template may be obtained and compared with a theoretical signal to determine the quality of the fit. In one example, a parameter or template may be adjusted and the profile model tested until termination criteria are met. According to a further exemplary process, if a measure of fit between the signals is below the termination criteria, i.e., the fit is not sufficiently good, a list of recommended actions may be produced for improving the model and increasing the fit. For example, a recommended action might include changing the model from a three-trapezoid model to a two-trapezoid model, allowing a variable to float, or the selection of a different template. The list of corrective actions may be listed in order of their respective likelihood for providing improvement to the profile model and the like. The list and order thereof may be generated by best-known methods for improving the signals, for example, based on prior experience and results from skilled and experienced users. In one example the user may manually select the recommended corrective action(s). Alternatively, the system may be programmed to automatically pick one or more corrective action(s), for example, the top two corrective actions. Further, any combination of a manual and automatic selection of corrective actions are possible.

When a corrective action is selected, the method or system modifies a parameter in the original template, e.g., a parameter may be changed or the range of a parameter value may be changed, and the modeling process may be repeated until the termination criteria are met. Alternatively, a new template may be chosen and the modeling process repeated. Each broad category template may further include multiple sub-templates with more specific parameters. If a change from 3 trapezoids to 2 trapezoids has the highest priority, switching to a particular sub-template may be appropriate. The sub-templates and the list of recommended actions preferably adapt over time to reduce iterations (i.e., adjustment of the parameters) of the model and parameter selection process. Further, templates and/or sub-templates may be adaptively created during use based on known and/or prior results of the system. Adjustments to the templates and list of recommended actions may be automatic, manual, or any combination thereof.

The use of templates and/or lists of recommended actions may reduce the trial and error of a model and parameter selection process by providing common starting points and recommending common corrective actions for a particular application. Further, selection of accurate profile models may be user-independent for common applications by minimizing the number of iterations to produce an acceptable profile model.

Figures 16, 18:
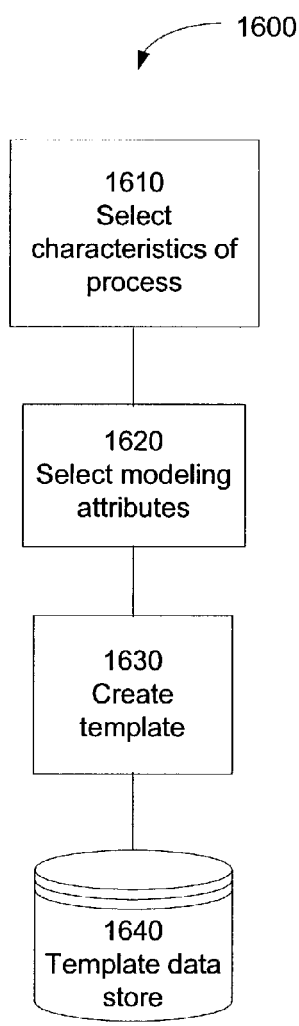
FIG. 16 is an exemplary process for creating templates for model and parameter selection for optical metrology of integrated circuit structures.
FIG. 18 is an exemplary list of recommended actions to modify parameters of the profile model.

FIG. 16 is an exemplary process 1600 for categorizing and creating templates for common applications that may be used in a process for model and parameter selection for an optical metrology system as described above with regard to FIG. 2 as well as other suitable modeling processes. In 1610 the characteristics of the process are determined for a particular application and wafer structures. For example, for a typical gate electrode, the characteristics of process might include the material(s) of a first layer, a second layer, a thin SiN film, a resist layer, a range of probable or expected thickness for each layer, and the like. There may be up to 50 or more parameters as will be appreciated by those skilled in the art.

In 1620 the modeling attributes associated with the application and wafer structure are selected for the template. Continuing with the example of a typical gate electrode, the parameters may include modeling parameters such as an ellipsometer (including both vendor and model), the range of wavelengths, the number of trapezoids used in the geometric model, and the like. The modeling attributes may be chosen for expected modeling parameters based, for example, on experience and prior modeling processes for similar applications. There may be up to 100 or more parameters as will be appreciated by those skilled in the art.

In 1630 the selected characteristics of process and modeling attributes selected in 1610 and 1630 are combined into a template corresponding to the application. Common applications for which templates might be created include, for example, wafer structures such as a metal shallow trench isolation, "metal STI," damascene, dual damascene, resist, silicon-on-insulator "SOI," and the like. A template consisting of a set of characteristics of process "A1," and a set of modeling attributes "B1," may then be stored as a template associated with a particular structure and/or process in 1640. For example, a metal shallow trench isolation structure may be represented by parameter sets A1, B1 where the parameters of A1, B1 are selected based on expected values or ranges of values for the different parameters based on the known structure and process. A dual damascene structure may be represented by parameter sets A2, B2, a gate electrode structure by A3, B3, and the like.

Further, the system may include sub-templates within or associated with a particular template to more particularly approximate the desired parameters. For example, within the gate electrode template, sub-templates A31, B31 and A32, B32 may be created for different aspects of gate electrode structures associated with different materials, processes, and the like. The sub-templates may be created and changed over time with use to adapt to common differences between a stored template and the corrections required to meet the termination criteria for the associated application. Both templates and/or sub-templates may further be ranked based on a priority scale of probability to fit a given structure within the main template such that a common application may be entered and a list of templates generated for a user or system to choose from.

Figure 17:
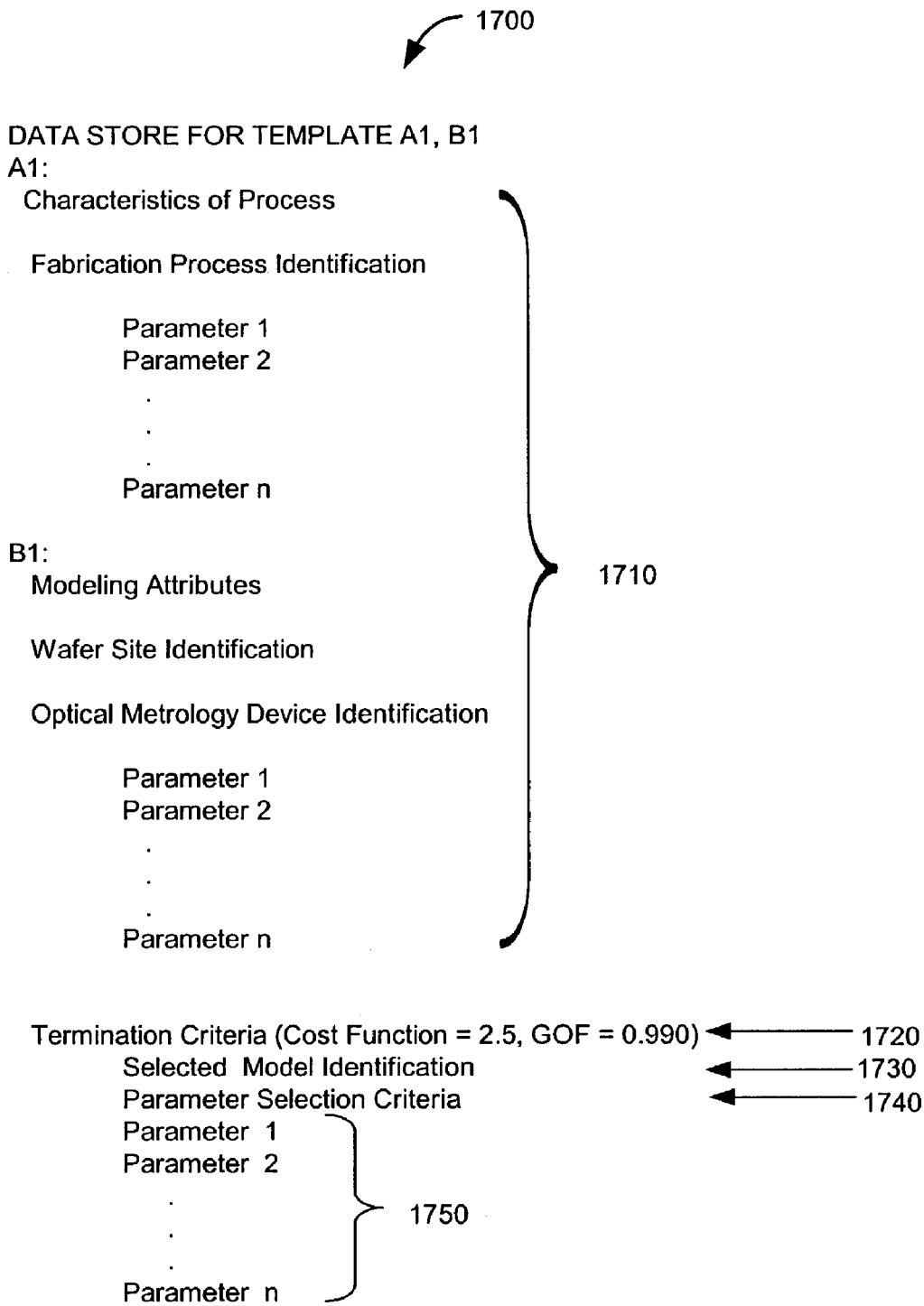
FIG. 17 is an exemplary template selection data store layout.

FIG. 17 includes an exemplary data storage layout for an exemplary template associated with a particular application. The data store format 1700 for a selected model and parameters associated with an application includes the fabrication process, wafer site, structure, and optical metrology device identification parameters listed as data 1710. The data store includes parameters for both the characteristics of process and the modeling attributes corresponding to the specific application.

The data store format 1700 may further include one or more data segments, each data segment optionally including the termination criteria 1720, selected model identification 1730, optimization parameter selection criteria 1740, and selected optimization parameters 1, 2, . . . n, 1750. Alternatively, the termination criteria 1720, selected model identification 1730, and optimization parameter selection criteria 1740 and selected optimization parameters 1750 may be entered or selected at the time of use.

The template may be associated, for example, with a metal STI application. The template may include a model identification of Shallow Trench Isolation Single Trapezoid Model, termination criteria may include a cost function of 1.5 and GOF of 0.995, optimization parameter selection criteria may include a correlation coefficient of 0.50 and sensitivity of 0.01 SSE, and the selected optimization parameters may include resist top CD, resist bottom CD, resist thickness, anti-reflective coating thickness, and silicon dioxide thickness. The termination criteria and optimization parameter criteria may be absent from a particular template, and a user or system may select the criteria during the profile modeling process.

According to another exemplary aspect, a list of recommended corrective actions may be generated to improve the modeling process. For example, if a modeling process based on a template fails to meet a set of termination criteria one or more actions may be selected from a list of recommended actions and the modeling process run with the modifications. FIG. 18 illustrates an exemplary list of recommended actions. In one example, a generalized recommended action list is generated and available for all templates. In another example, recommended action lists are customized or associated with particular templates to increase the accuracy of the actions.

The list or recommended actions may be created and/or prioritized based, at least in part, on best-known methods for improving goodness of fit metrics, common errors in initial parameter information, historical data, profile model testing, and the like. In one example, the priority of recommended actions is based on process knowledge and results of the modeling process, i.e., which parameters have a poor fit, correlation, and the like.

Recommended actions may include actions such as change model from 3-trapezoids to 2-trapezoids (see FIGS. 13A–13D), from a fixed pitch to float the pitch between periodic structure, modify highly correlated variables or parameters, change model to include a thin polymer layer over the structure, or select a different template. For example, the pitch of a periodic structure is often incorrectly provided. Altering the model to allow the pitch to vary or float within a range may improve the fit metrics. Further, structures often have a thin polymer layer deposited over the structure that is unaccounted for, such that by including this layer in the model the fit metrics are improved.

Further, the priority assigned to a recommended action may change over time or the fabrication process. For example, in an STI structure, fixing a certain parameter may initially be a high priority recommended action, but over time may prove ineffective in improving the profile model and reduced accordingly to a lower priority action. In comparison, a damascene structure may always have high priority for to changing the geometrical model based on known variations in the structure. Thus, the list of recommended actions may be adaptive over time based on successful (and unsuccessful) actions taken, i.e., did the selected action(s) improve and/or meet the termination criteria. Additionally, the templates may similarly adapt over time based on the number of iterations of modifying parameters in the template performed to meet the termination criteria or the like.

Figure 19:
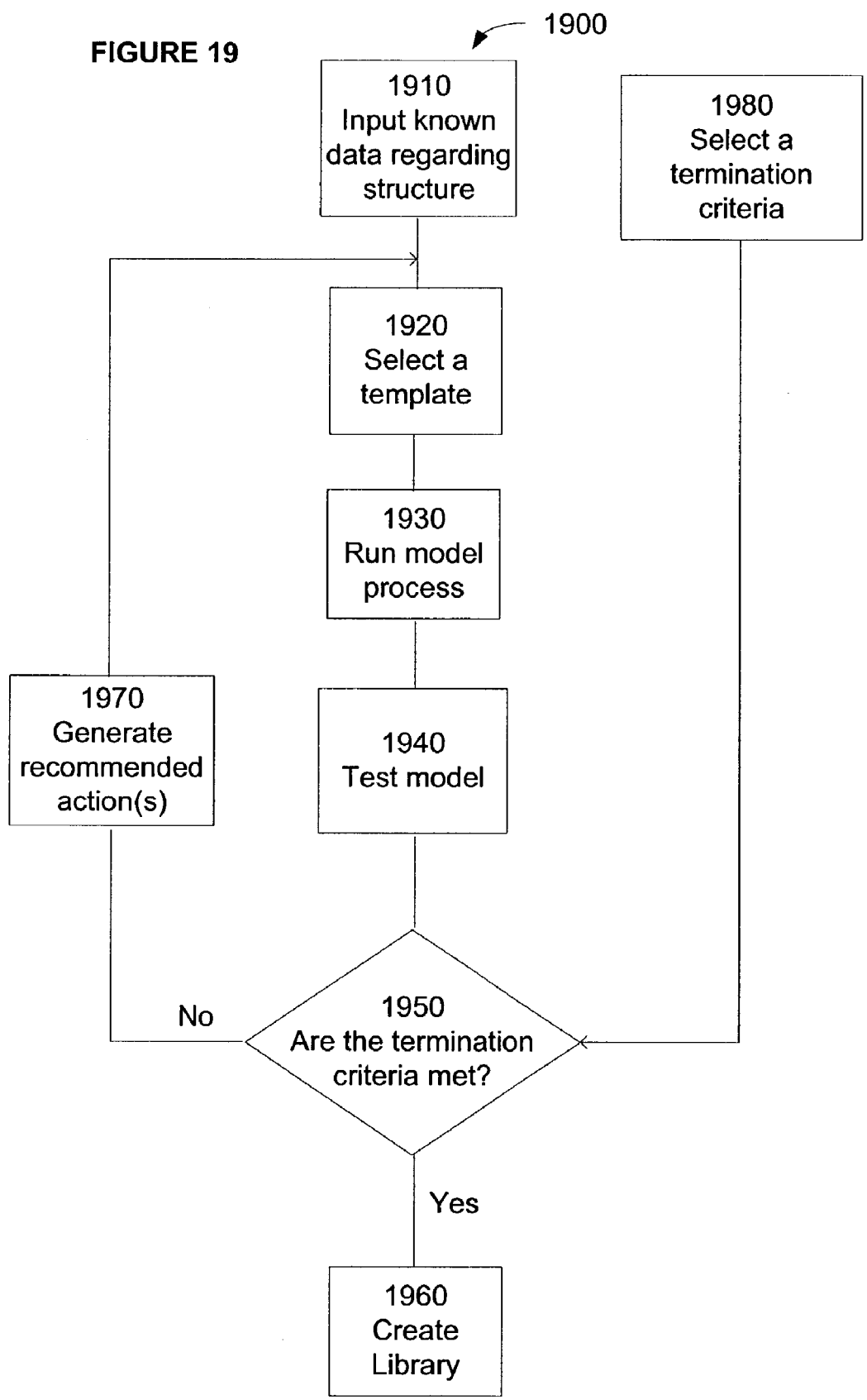
FIG. 19 is an exemplary process for using templates for model and parameter selection for optical metrology of integrated circuit structures.

FIG. 19 is an exemplary process for model and parameter selection for optical metrology of wafer structures including application specific templates. The exemplary process 1900 utilizes application specific templates with expected or likely parameter values for common applications. The exemplary process may further produce recommended actions such as changes to the model or deletion of specific parameters in instances where the termination criteria are not met, i.e., the model fit is not within a desired range, that may be selected automatically, manually, or a combination thereof.

In 1910 known data regarding a wafer structure is retrieved such as the fabrication characteristics, type of wafer structure, and the like which indicate the likely characteristics of the wafer structure. An appropriate template associated with the application including expected characteristics of process and likely modeling attributes for that application may be selected at 1920 to create a starting point in the model and parameter selection process.

In 1930 the profile model is run based on the selected template associated with the wafer structure. One exemplary profile model process is described in greater detail with regard to FIG. 2; however, it should be understood that other profile model and parameter selection processes may be used with this embodiment of the invention. After the profile model process is run, a model fit metric indicative of the closeness of the profile model fit is determined by testing the profile model at 1940. The termination criteria for the model metric may be selected in 1980 and used to determine if the termination criteria are met at 1950. The model metric and termination criteria may include one or more modeling metrics including, for example, a cost function, goodness of fit value, confidence interval, and the like.

In one example, a weighting or point system of several model fit metrics may be used to determine if action needs to be taken to improve the template parameters. For example, values for model fit metrics such as sensitivity, noise, and correlation may be assigned points depending on the quality of the fit. The values from different metrics may then be cumulated and compared to a threshold value and if the value exceeds the threshold value the model is sufficient and further modification to the parameters and/or template is unnecessary.

In an instance where the termination criteria have been met at 1950, a library of simulated diffraction signals and structure profiles may be created at 1960, for example, as described with respect to FIGS. 2 and 6A. Further, the results of the model profile and parameter selections may be displayed, used for fabrication cluster loop control, and the like.

According to one example, if the termination criteria are not met at 1950, then the process produces a list of recommended actions to improve the model metric(s) at 1970. One or more of the recommended actions may be chosen and the profile model process run again. The process may continue for several iterations until the termination criteria are satisfied. The list of recommended actions may be prioritized by the probability of an action improving the model and model metric(s). The action may include changing a parameter, allowing a parameter to float (i.e., not fixed), selecting a new template or sub-template, and the like. Further, one or more of the actions may be chosen for each iteration, for example, choosing the first and second recommended actions and the like.

Figure 20:
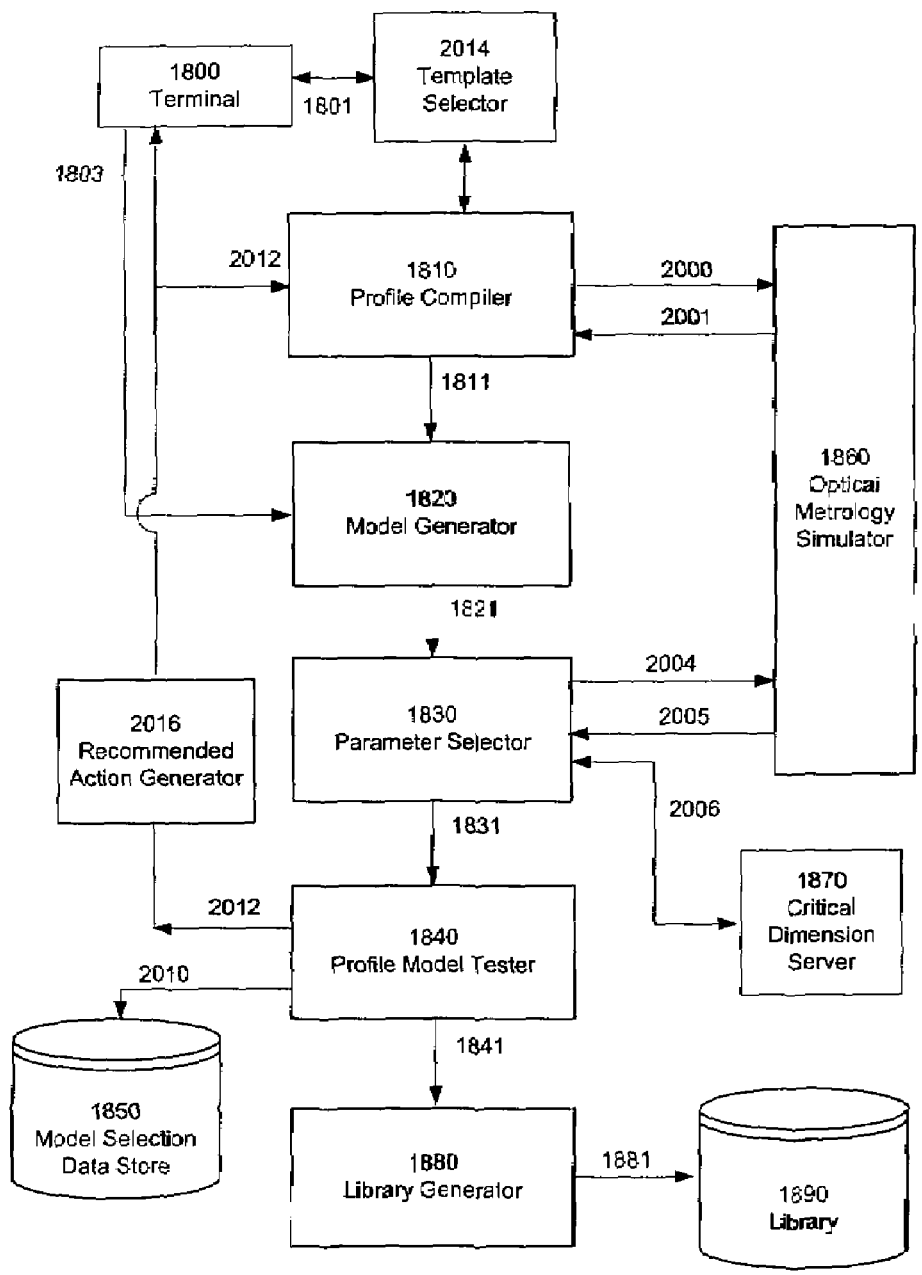
FIG. 20 is an architectural diagram depicting an exemplary system for model and parameter selection.

FIG. 20 is an architectural diagram depicting a system for model and parameter selection in one exemplary embodiment. FIG. 20 is similar to FIG. 6A with the addition of a template selector 2014 and a recommended action generator 2016. Accordingly, those details previously discussed will be omitted with respect to the description of FIG. 20. It should be recognized a template selector and/or recommended action generator may be used with various other modeling systems.

Wafer fabrication process design and structure data associated with the particular application may be entered at terminal 1800. For example, the input may include the broad category of the process and structure as well as the stack, n and k values, nominal profile parameter values and ranges, width nominal values and ranges, measured diffracted signals off several sites in the wafer, and structure image data to characterize the structure profile. The input data 1801 may then be transmitted so template selector 2014 where an appropriate template is selected for use. The template selector 2040 may select a template from a template data store 1806 based on a match of the category name, a best-fit match of inputted data or parameters, or any other suitable method.

Profile compiler 1810, model generator 1820, parameter selector 1830, and profile model tester 1840 may operate similarly to FIG. 6A. Template selector 2014 may further provide data such as the selection of optimization parameters, termination criteria, and the like.

If the termination criteria are not met in profile model tester 1840, recommended action generator 2016 produces a list of recommended actions, e.g., prioritized according to the potential to increase the quality of the profile model to meet the termination criteria. In one example, the output of recommended action generator 2016 may automatically select one or more of the actions and send the action to the profile compiler to begin a new model process. In another example, the output may be returned to terminal 1800 such that a user may select an action from recommended action generator 2016. The system may then repeat the model generation process based on any changes made until the termination criteria are met.

It is contemplated that functional implementation of the exemplary embodiments described herein may be implemented equivalently in hardware, software, firmware, and/or other available functional components or building blocks. Other variations and embodiments are possible in light of above teachings, and it is thus intended that the scope of invention is not be limited by the Detailed Description, but rather by Claims following.

We claim:

1. A method of selecting a profile model and selecting parameters of the profile model for use in optical metrology of structures in a wafer, the method comprising:
   a) selecting a template associated with a wafer structure from a plurality of templates, the template having one or more parameters based on:
      characteristics of process, and
      profile modeling attributes for use in optical metrology of a structure in a wafer; and
   b) generating a profile model characterizing the wafer structure based on the one or more parameters of the selected template.

2. The method of claim 1, further including testing the profile model to generate a model fit metric, and generating a list of actions to improve the profile model against the model fit metric wherein the list of actions includes at least one of:
   modifying at least one of the one or more parameters, and
      selecting a new template.

3. The method of claim 2, wherein the list of actions is generated based on the selected template.

4. The method of claim 2, further including selecting at least one of the actions to improve the profile model based on a predetermined selection rule.

5. The method of claim 2, wherein generating a list of actions to improve the profile modeling process adapts through use based on actions that improve the profile modeling process.

6. The method of claim 1, wherein the characteristics of process include at least one of characterizations of the wafer structure, wafer fabrication process, wafer layer stack, design nominal dimensions of the wafer structure, and expected ranges of dimensions of the wafer structure.

7. The method of claim 1, wherein the profile modeling attributes include at least one off expected geometric shapes of the structure, geometric parameters, nominal values of geometric parameters, and ranges of geometric parameters.

8. The method of claim 1, further including:
   c) determining one or more termination criteria;
   d) determining if the one or more termination criteria are met by the generated profile model; and
   e) modifying at least one of the one or more parameters and repeating b), d), and e) until the one or more termination criteria are met.

9. The method of claim 8, further including generating a list of actions to improve the profile model against a model fit metric, wherein the modifying the at least one of the one or more parameters includes selecting one or more of the actions to improve the profile model.

10. The method of claim 9, wherein the list of actions are listed in an order based on a probability for meeting the one or more termination criteria.

11. The method of claim 8, wherein the template adapts based on the number of times b), d), and e) are repeated.

12. The method of claim 8, wherein the termination criteria include a weighting system of at least one of sensitivity, noise, and correlation values of the profile model.

13. A method of selecting a profile model and selecting parameters of the profile model for use in optical metrology of structures in a wafer, the method comprising:
   a) setting one or more termination criteria;
   b) setting one or more parameter selection criteria;
   c) selecting a template associated with a wafer structure from a plurality of templates, the template having one or more parameters based on characteristics of process and modeling attributes;
   d) selecting a profile model for use in optical metrology of a structure in a wafer, the profile model including geometric parameters associated with dimensions of the wafer structures;
   e) selecting a set of optimization parameters for the profile model using one or more input diffraction signals and the one or more parameter selection criteria, wherein the set of optimization parameters is converted from the set of geometric parameters;
   f) testing the profile model and the act of optimization parameters against the one or more termination criteria; and
   g) modifying one or more of the parameters based on characteristics of process and modeling attributes and repeating d), e), and f) if the one or more termination criteria are not met.

14. The method of claim 13, further including generating a list of actions to improve the selected profile model with respect to the termination criteria and selecting one or more of the actions when modifying the one or more parameters.

15. The method of claim 13, wherein testing the profile model and the set of optimization parameters against the one or more termination criteria includes:
   testing if a simulated diffraction signal cost function value is less than or equal to a preset cost function value, the simulated diffraction cost function value calculated by comparing an optimized simulated diffraction signal to a measured diffraction signal.

16. The method of claim 13, wherein testing the profile model and the set of optimization parameters against the one or more termination criteria includes:
   testing if a simulated diffraction signal goodness of fit value is equal to or greater than a preset goodness of fit value, the simulated diffraction signal goodness of fit value calculated by comparing an optimized simulated diffraction signal to a measured diffraction signal.

17. The method of claim 13, wherein testing the profile model and the set of optimization parameters against the one or more termination criteria includes:
   testing if one or more calculated confidence interval values are less than or equal to corresponding preset confidence interval values, the confidence interval being a range of values of an optimization parameter within which an actual value is expected to fall within a specified probability.

18. The method of claim 13, wherein testing the profile model and the set of optimization parameters against the one or more termination criteria includes:
   testing if a simulated diffraction signal cost function value is less than or equal to a preset cost function value, the simulated diffraction cost function value calculated by comparing an optimized simulated diffraction signal to a measured diffraction signal; and
   testing if the simulated diffraction signal goodness of fit value is equal to or greater than a preset goodness of fit value, the simulated diffraction signal goodness of fit value calculated by comparing the best match simulated diffraction signal to the measured diffraction signal.

19. The method of claim 18, wherein testing the profile model and the set of optimization parameters against the one or more termination criteria includes:
   testing if one or more calculated confidence interval values are less than or equal to corresponding preset confidence interval values, the confidence interval being a range of values of an optimization parameter within which an actual value is expected to fall within a specified probability.

20. The method of claim 13, wherein the one or more parameter selection criteria comprise:
   a correlation cutoff, the correlation cutoff being a correlation coefficient between an optimization parameter and another optimization parameter of the profile model;
   a sensitivity threshold of an optimization parameter, the sensitivity threshold being the sum-squared-error of a first simulated diffraction signal calculated using nominal values for all the optimization parameters compared to a second simulated diffraction signal calculated using an adjusted value of the optimization parameter and nominal values for all the other optimization parameters, the adjusted value of the parameter being the nominal values plus or minus an increment; and
   a confidence interval threshold of an optimization parameter, the confidence interval threshold being the amount of change from the nominal value of an optimization parameter that results in a change in the simulated diffraction signal greater than a measured or simulated noise level for the optimization parameter, the rest of the optimization parameters being held constant at respective nominal values.

21. The method of claim 13, wherein selecting the set of optimization parameters for the profile model using one or more input diffraction signals and the one or more parameter selection criteria further comprises:
    selecting wavelengths for optical metrology;
    calculating values of the one or more parameter selection criteria;
    selecting optimization parameters that meet the one or more parameter selection criteria; and
    performing a procedure to determine an optimized simulation diffraction signal corresponding to a measured diffraction signal using the selected optimization parameters of the profile model.

22. The method of claim 21, wherein selecting wavelengths for optical metrology comprises:
    selecting wavelengths that meet a noise level criteria, the noise level being a standard deviation of diffraction signals off a same site in a wafer; and
    selecting wavelengths that have low correlation of diffraction signals compared to diffraction signals of other wavelengths.

23. The method of claim 21, wherein selecting optimization parameters that meet the one or more parameter selection criteria includes:
    selecting optimization parameters that meet a correlation cutoff, the correlation cutoff being a preset correlation coefficient value of simulated diffraction signals between an optimization parameter and another optimization parameter of the profile model.

24. The method of claim 21, wherein selecting optimization parameters that meet the one or more parameter selection criteria includes:
    selecting optimization parameters that meet a sensitivity threshold of an optimization parameter, the sensitivity threshold being the sum-squared-error of a first simulated diffraction signal calculated using nominal values for all the optimization parameters compared to a second simulated diffraction signal calculated using an adjusted value of the optimization parameter and nominal values for all the other optimization parameters, the adjusted value of the optimization parameter being the nominal value plus or minus an increment.

25. The method of claim 21, wherein selecting optimization parameters that meet the one or more parameter selection criteria includes:
    selecting optimization parameters that meet a confidence interval threshold, the confidence interval threshold being the amount of change from the nominal value of an optimization parameter that results in a change in the simulated diffraction signal greater than a measured or simulated noise level for the optimization parameter, the rest of the optimization parameters being held constant at respective nominal values.

26. The method of claim 21, wherein performing the procedure to determine the optimized simulation diffraction signal corresponding to the measured diffraction signal using the selected optimization parameters of the profile model further comprises:
    utilizing an optimization procedure to find the simulation diffraction signal that yields the least error compared to the measured diffraction signal.

27. The method of claim 26 wherein the optimization procedure utilizes one or more global optimization techniques including branch-and-bound technique, simulated annealing, genetic algorithm, other global optimization technique or hybrid global and local optimization technique.

28. The method of claim 13, further comprising:
    saving into a data store identification data associated with the structure, the wafer, and the selected model and data about the termination criteria, the one or more parameter selection criteria, and the selected optimization parameters.

29. A method of determining wafer structure having critical dimensions, profile shape, and film thickness using optical metrology, the method comprising:
    a) setting one or more termination criteria;
    b) setting one or more parameter selection criteria;
    c) selecting a template associated with a wafer structure from a plurality of templates having one or more parameters for generating a profile model for use in optical metrology of a structure in a wafer,
    d) selecting a profile model having a set of geometric parameters associated with dimensions of the structure including critical dimensions, profile shape, and film thickness;
    e) selecting a set of optimization parameters for the profile model using one or more input diffraction signals and the one or more parameter selection criteria, wherein the set of optimization parameters is converted from the set of geometric parameters;
    f) testing the selected profile model and the set of optimization parameters against the one or more termination criteria;
    g) modifying the template and performing d) and e) if the one or more termination criteria are not met; and
    h) assessing critical dimensions, profile shape, and film thickness associated with the selected profile model and selected optimization parameters of the selected profile model.

30. The method of claim 29, further comprising:
    displaying critical dimensions, profile shape, and film thickness associated with the one or more diffraction signals.

31. The method of claim 29, further comprising:
    creating a library of diffraction signals and associated profile data using the selected optimization parameters of the selected profile model.

32. A system for processing optical metrology data for wafer structures, the system comprising:
    a model generator configured to generate a profile model for a structure in a wafer using characterizations of the structure and to process one or more termination criteria and one or more parameter selection criteria;
    a template selector configured to select a template including parameters for the profile model based on the characteristics of process and modeling attributes of the wafer structure;
    an optical metrology simulator configured to use the profile model and selected optimization parameter values to calculate a simulated diffraction signal;
    a parameter selector coupled to the model generator and to the optical metrology simulator, the parameter selector configured to perform calculations of one or more parameter selection criteria values, to compare the calculated one or more parameter selection criteria values to the one or more parameter selection criteria, and to select optimization parameters that meet the one or more parameter selection criteria; and
    a profile model tester coupled to the parameter selector, the profile model tester configured to perform calculations of termination values, to compare the calculated termination values to the one or more termination criteria, and to adjust the profile model if the one or more termination criteria are not met.

33. The system of claim 32, further comprising:
a recommended action generator coupled to the profile model tester and configured to produce a list of recommended actions to meet the termination criteria.

34. The system of claim 32, further comprising:
a profile compiler coupled to the optical metrology simulator, to the model generator, and to the profile model tester, the profile compiler configured to process input data including characterizations of the wafer structure, wafer fabrication process, wafer layer stack, design nominal dimensions of wafer structure, and expected ranges of dimensions of the wafer structures.

35. The system of claim 32, further comprising:
a data store coupled to the profile model tester, the data store configured to store identification data associated with the structure, the wafer, and the selected model and data about the termination criteria, the one or more parameter selection criteria, and the selected optimization parameters.

36. The system of claim 32, further comprising:
a library generator coupled to the profile model tester and the optical metrology simulator, the library generator configured to utilize structure profile data from the profile model tester and invoke the optical metrology simulator to calculate simulated diffraction signals.

37. The system of claim 32, further comprising:
a library coupled to the library generator, the library configured to contain diffraction signals and associated structure profile data.

38. The system of claim 32, wherein the profile model tester further comprises:
one or more optimization engines configured to utilize one or more global optimization algorithms including branch-and-bound technique, simulated annealing, genetic algorithm, other global optimization technique or hybrid global and local optimization technique.

39. The system of claim 32, further comprising:
a terminal coupled to the profile compiler and to the model generator, the terminal configured to:
accept input data including characterizations of the wafer structure, wafer fabrication process, wafer layer stack, design nominal dimensions of wafer structure; expected ranges of dimensions of the wafer structures; and
accept specification of geometric shapes for profile models and dependencies of parameters of the geometric shapes.

40. The system of claim 39, further comprising:
a critical dimension server coupled to the parameter selector, the critical dimension server configured to display structure data including critical dimensions, structure profile, and film thickness corresponding to measured diffraction signals.

41. A system for real-time determination of profile data of wafer structures, the system comprising:
an optical metrology system configured to measure diffraction signals off wafer structures;
a metrology model optimizer coupled to the optical metrology system, the metrology model optimizer configured to:

process the characterization of wafer structure profiles, the metrology model specifications, one or more termination criteria, and one or more parameter selection criteria;
select a template associated with the wafer structure and including one or more parameters including characteristics of process and modeling attributes;
generate one or more profile models of the wafer structures, the profile models having associated parameters;
select parameters of the profile model, the selected parameters meeting the one or more selection criteria, and
generate a list of recommended actions to modify at least one of the one or more parameters to improve the profile model;
perform the generation of one or more profile models and selection of parameters of the model, the selected parameters meeting the one or more parameter selection criteria until the one or more termination criteria are met;
a profiler workstation coupled to the metrology model optimizer, the profiler workstation configured to:
receive input regarding the wafer structure profiles, the metrology model specifications, the one or more termination criteria, and the one or more parameter selection criteria; and
display output information comprising critical dimensions, profile shape, and film thickness of the wafer structures; and
a data store coupled to the profile model tester, the data store configured to:
store identification data associated with the structure, the wafer, and the selected model and data about the termination criteria, the one or more parameter selection criteria, and the selected optimization parameters.

42. The system of claim 41, further comprising:
a fabrication cluster coupled to the optical metrology system and the metrology model optimizer, the fabrication cluster configured to:
perform one or more processes in the manufacture of wafers and wafer structures.

43. A computer-readable storage medium containing computer executable code to select a profile model for use in integrated circuit optical metrology by instructing a computer to operate as follows:
a) selecting a template associated with a wafer structure from a plurality of templates, the template having one or more parameters based on the characteristics of process and profile modeling attributes for use in optical metrology of a structure in a wafer; and
b) performing a profile modeling process based on the one or more parameters of the selected template to generate a profile model.

44. The computer-readable storage medium of claim 43, further including testing the profile model to generate a model fit metric, and generating a list of actions to improve the profile model against the model fit metric, the list of actions including at least one of modifying one or more parameters of the template and selecting a new template.

45. The computer-readable storage medium of claim 44, further including selecting at least one of the one or more actions to improve the profile model based on a predetermined selection rule.

46. The computer-readable storage medium of claim 43, further including:
  c) determining one or more termination criteria;
  d) determining if the one or more termination criteria are met by the generated profile model; and
  e) modifying at least one of the one or more parameters and repeating b), d), and e) if the one or more termination criteria are not met.

* * * * *